(12) United States Patent
Cox et al.

(10) Patent No.: US 10,323,231 B2
(45) Date of Patent: *Jun. 18, 2019

(54) ATTENUATED INFLUENZA VACCINES AND USES THEREOF

(71) Applicant: UNIVERSITY OF ROCHESTER, Rochester, NY (US)

(72) Inventors: Andrew Cox, Rochester, NY (US); Stephen Dewhurst, Rochester, NY (US); John Treanor, Fairport, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/568,836

(22) PCT Filed: Apr. 22, 2016

(86) PCT No.: PCT/US2016/028992
§ 371 (c)(1),
(2) Date: Oct. 24, 2017

(87) PCT Pub. No.: WO2016/172588
PCT Pub. Date: Oct. 27, 2016

(65) Prior Publication Data
US 2018/0223261 A1    Aug. 9, 2018

Related U.S. Application Data

(60) Provisional application No. 62/152,276, filed on Apr. 24, 2015.

(51) Int. Cl.
*C12N 7/00*   (2006.01)
*C12N 9/12*   (2006.01)
*A61K 39/00*  (2006.01)
*A61K 39/12*  (2006.01)
*A61P 31/16*  (2006.01)
*A61K 39/145* (2006.01)
*C07K 14/005* (2006.01)

(52) U.S. Cl.
CPC ............... *C12N 7/00* (2013.01); *A61K 39/12* (2013.01); *A61K 39/145* (2013.01); *A61P 31/16* (2018.01); *C07K 14/005* (2013.01); *C12N 9/127* (2013.01); *C12Y 207/07048* (2013.01); *A61K 2039/5254* (2013.01); *C12N 2760/16122* (2013.01); *C12N 2760/16134* (2013.01); *C12N 2760/16151* (2013.01); *C12N 2760/16162* (2013.01); *C12N 2760/16171* (2013.01)

(58) Field of Classification Search
CPC .................. C12N 7/00; C12N 9/127; C12N 2760/16151; C12N 2760/16171; C12N 2760/16162; C12N 2760/16134; C12N 2760/16122; C12Y 207/07048; A61K 39/145; A61K 39/12; A61K 2039/5254; C07K 14/005; A61P 31/16
See application file for complete search history.

(56) References Cited

U.S. PATENT DOCUMENTS

| | | | |
|---|---|---|---|
| 8,354,114 B2 | 1/2013 | Lu et al. | |
| 9,878,032 B2 * | 1/2018 | Cox | ............... A61K 39/145 |
| 2003/0099670 A1 | 5/2003 | Hobom et al. | |
| 2004/0029251 A1 | 2/2004 | Hoffman et al. | |
| 2005/0266026 A1 | 12/2005 | Hoffmann et al. | |
| 2008/0292658 A1 | 11/2008 | De Wit et al. | |
| 2009/0074804 A1 | 3/2009 | Lee et al. | |
| 2011/0150912 A1 | 6/2011 | Perez | |
| 2013/0115242 A1 | 5/2013 | Moules et al. | |
| 2015/0224187 A1 | 8/2015 | Cox et al. | |
| 2016/0136260 A1 | 5/2016 | Cox et al. | |

FOREIGN PATENT DOCUMENTS

| | | | | |
|---|---|---|---|---|
| WO | WO-2014086732 A2 * | 6/2014 | ............ | A61K 39/145 |
| WO | WO-2015010073 A1 * | 1/2015 | ............. | C12N 9/127 |

OTHER PUBLICATIONS

Betts MJ, Russell RB. "Amino Acid Properties and Consequences of Substitutions." In "Bioinformatics for Geneticists." Eds. Barnes MR, Gray IC. 2003. John Wiley & Sons, Ltd.*
"RNA-directed RNA Polymerase Catalytic Subunit", UniProtKB—Q9ICX7(Q9ICX7_9INFA), Oct. 1, 2000, 7 pages.
"RNA-Directed RNA Polymerase Catalytic Subunit", UniProtKB—Q9WLS3 (RDRP 197A1), Dec. 6, 2005, 6 pages.
Chinese Patent Application No. CN201480045309.0, "Office Action", dated Jul. 24, 2018 (6 pages in Chinese and 3 pages of English translation).
Shilei Ding et al., "流感冷适应减毒活疫苗的研究进展", Chin J. Biologicals, vol. 20, No. 11, Nov. 2007, pp. 866-868 (3-page article published in Chinese that describes the development of cold-adapted live attenuated influenza virus vaccine and 1 page English description).
Ambrose et al., "The efficacy of live attenuated and inactivated influenza vaccines in children as a function of time postvaccination", Pediatr. Infect. Dis. J., vol. 29, 2010, pp. 806-811.
Ambrose et al., "The safety and efficacy of live attenuated influenza vaccine in young children with asthma or prior wheezing", Eur J. Clin MicrobiolInfect Dis., vol. 31, 2012, pp. 2549-2557.
Ambrose et al., "The relative efficacy of trivalent live attenuated and inactivated influenza vaccines in children and adults", Influenza Other Respir Viruses, 2011, vol. 5, pp. 67-75.
Baker et al., "Protection against lethal influenza with a viral mimic", J. Virol, vol. 87, 2013, pp. 8591-8605.
Belshe et al., "Efficacy of live attenuated influenza vaccine in children 6 months to 17 years of age", Influenza Other Respir Viruses, vol. 4, 2010, pp. 141-145.
Belshe et al., "Safety and efficacy of live attenuated influenza vaccine in children 2-7 years of age", Vaccine, vol. 26, Issue 4, 2008, pp. D10-D16.

(Continued)

*Primary Examiner* — Rachel B Gill
(74) *Attorney, Agent, or Firm* — Kilpatrick Townsend & Stockton LLP

(57) ABSTRACT
Provided herein are attenuated influenza viruses and methods of making attenuated influenza viruses.

24 Claims, 18 Drawing Sheets

Specification includes a Sequence Listing.

(56) References Cited

OTHER PUBLICATIONS

Belshe et al., "Live attenuated versus inactivated influenza vaccine in infants and young children", N Engl J Med, 2007, vol. 356, pp. 685-696.
Belshe et al., "Safety and efficacy of live attenuated, cold-adapted, influenza vaccine-trivalent", Immunol Allergy Clin North Am, 2003, vol. 23, pp. 745-767.
Belshe et al., "The efficacy of live attenuated, cold-adapted, trivalent, intranasal influenzavirus vaccine in children", N Engl J Med, 1998, vol. 338, pp. 1405-1412.
Block et al., "Shedding and immunogenicity of live attenuated influenza vaccine virus in subjects 5-49 years of age", Vaccine, vol. 26, 2008, pp. 4940-4946.
Bowie et al., Deciphering the Message in Protein Sequences: Tolerance to Amino Acid Substitutions, Science, 247, 1990, pp. 1306-1310.
Brooke et al., "Most Influenza A Virions Fail to Express at Least One Essential Viral Protein", Journal of Virology, vol. 87, No. 6, Mar. 15, 2013, pp. 3155-3162.
Bussey et al., "PA residues in the 2009 H1 N1 pandemic influenza virus enhance avian influenza virus polymerase activity in mammalian cells", J. Viral., vol. 85, Issue 14, 2011, pp. 7020-7028.
Carter et al., "Live attenuated influenza vaccine (FluMist(R); Fluenz): a review of its use in the prevention of seasonal influenza in children and adults", Drugs, vol. 71, 2011, pp. 1591-1622.
Cha et al., "Genotypic stability of cold-adapted influenza virus vaccine in an efficacy clinical trial", J. Clin. Microbial., vol. 38, 2000, pp. 839-845.
Chan et al., "The cold adapted and temperature sensitive influenza A/Ann Arbor/6/60 virus, the master donor virus for live attenuated influenza vaccines, has multiple defects in replication at the restrictive temperature", Virology, vol. 380, 2008, pp. 304-311.
Chen et al., "Safety, immunogenicity, and efficacy of a cold-adapted A/Ann Arbor/6/60 (H2N2) vaccine in mice and ferrets", Virology, vol. 398, 2010, pp. 109-114.
Chew et al., "Characterization of the interferon regulatory factor 3-mediated antiviral response in a cell line deficient for IFN production", Mol Immunol., 2009, vol. 46, pp. 393-399.
Cox et al., "Development of a Mouse-Adapted Live Attenuated Influenza Virus That Permits In Vivo Analysis of Enhancements to the Safety of Live Attenuated Influenza Virus Vaccine", Journal of Virology, vol. 89, Issue 6, Mar. 2015, pp. 3421-3426.
Cox et al., "Identification of sequence changes in the cold-adapted, live attenuated influenza vaccine strain, A/Ann Arbor/6/60 (H2N2)", Virology, vol. 167, 1988, pp. 554-567.
Cox et al., A Single Mutation at PB1 Residue 319 Dramatically Increases the Safety of PR8 Live Attenuated Influenza Vaccine in a Murine Model without Compromising Vaccine Efficacy, J. Virol., vol. 90, No. 5, Mar. 2016, pp. 2702-2705.
Da Costa et al., "Temperature-sensitive mutants in the influenza A virus RNA polymerase: alterations in the PA linker reduce nuclear targeting of the PB1-PA dimer and hence result in viral attenuation", J. Virol. Doi:10.1128/JVI.00589-15, Apr. 8, 2015, 47 pages.
Database UniProt, "RecName: Full=RNA-directed RNA polymerase catalytic subunit {ECO:0000256:RuleBase:RU004330, ECO:0000256:SAAS:SAAS00509014}; EC=2.7.7.48 {ECO:0000256:RuleBase:RU004330, ECO:0000256:SAAS:SAAS00508944}", XP002756978, Database accession No. Q9ICX7, Oct. 2000, 3 pages.
Database UniProt, "RecName: Full=RNA-directed RNA polymerase catalytic subunit; EC=2.7.7.48; AltName: Full=Polymerase basic protein 1; Short=PB1; AltName: Full=RNA-directed RNA polymerase subunit P1", XP002756977, Database accession No. Q9WLS3, Dec. 6, 2005, 3 pages.
Emeny et al.,"Refulation of the interferon system: evidence that Vero cells have a genetic defect in interferon production", J Gen Virol, 1979, vol. 43, pp. 247-252.
European Patent Application No. 14827095.2, Extended European Search Report, dated May 13, 2016, 11 pages.

European Patent Application No. 14827095.2, Office Action, dated Jan. 24, 2018, 4 pages.
European Patent Application No. 14827095.2, Office Action, dated May 31, 2017, 6 pages.
Garaigorta et al., "Genetic analysis of influenza virus NS1 gene: a temperature-sensitive mutant shows defective formation of virus particles", J. Virol, vol. 79, 2005, pp. 15246-15257.
Genbank Accession No. AY210012.1, https://www.ncbi.nlm.nih.gov/nuccore/AY210012.1.
Genbank Accession No. GQ377049.1, https://www.ncbi.nlm.nih.gov/nuccore/GQ377049.1.
Genbank Accession No. KC883051.1, https://www.ncbi.nlm.nih.gov/nuccore/KC883051.1.
Genbank Accession No. AF156421.1, https://www.ncbi.nlm.nih.gov/nuccore/AF156421.1.
Genbank Accession No. AF156435.1, https://www.ncbi.nlm.nih.gov/nuccore/AF156435.
Genbank Accession No. KF021594.1, https://www.ncbi.nlm.nih.gov/nuccore/KF021594.
Genbank Accession No. AY180761.1, https://www.ncbi.nlm.nih.gov/nuccore/AY180761.
Genbank Accession No. AY209938.1, https://www.ncbi.nlm.nih.gov/nuccore/AY209938.1.
Govorkova et al., "Growth and immunogenicity of influenza viruses cultivated in Vero or MDCK cells and in embryonated chicken eggs", Dev Biol Stand, 1999, vol. 98, pp. 39-51.
Govorkova et al., "African green monkey kidney (Vero) cells provide an alternative host cell system for influenza A and B viruses", J Virol, 1996, vol. 70, pp. 5519-5524.
Grimm et al., "Replication fitness determines high virulence of influenza A virus in mice carrying functional Mx1 resistance gene", Proc Natl Acad Sci USA, vol. 104, 2007, pp. 6806-6811.
Grohskopf et al., "Prevention and Control of Seasonal Influenza with Vaccines: Recommendations of the Advisory Committee on Immunization Practices (ACIP)", Centers for Disease Control and Prevention. vol. 63(32), Aug. 15, 2014, pp. 691-697.
Halliley et al., "High-affinity H7 head and stalk domain-specific antibody responses to an inactivated influenza H7N7 vaccine after priming with live attenuated influenza vaccine", J Infect Dis, 2015, vol. 212, pp. 1270-1278.
Jin et al., "Imparting temperature sensitivity and attenuation in ferrets to A/Puerto Rico/8/34 influenza virus by transferring the genetic signature for temperature sensitivity from cold-adapted A/Ann Arbor/6/60", J. Virol, vol. 78, 2004, pp. 995-998.
Jin et al., "Multiple amino acid residues confer temperature sensitivity to human influenza virus vaccine strains (FluMist) derived from cold-adapted A/Ann Arbor/6/60", Virology, vol. 306, 2003, pp. 18-24.
Kilbourne, "Future influenza vaccines and the use of genetic recombinants", Bull World Health Organ, vol. 41, 1969, pp. 643-645.
Kistner et al., "Development of a mammalian cell (Vero) derived candidate influenza virus vaccine", Vaccine 1998, vol. 16, pp. 960-968.
Klein et al., "Behavioral thermoregulation in mice inoculated with influenza virus", Physiol Behav, vol. 52, 1992, pp. 1133-1139.
Krammer et al., "Assessment of influenza virus hemagglutinin stalk-based immunity in ferrets", J. Virol., vol. 88, 2014, pp. 3432-3442.
Krammer et al., "Influenza virus hemagglutinin stalk-based antibodies and vaccines", Curr Opin Virol., vol. 3, 2013, pp. 521-530.
Lin et al., "Avian-to-human transmission of H9N2 subtype influenza A viruses: relationship between H9N2 and H5N1 human isolates", Proc Natl Acad Sci, vol. 97, No. 17, Aug. 15, 2000, pp. 9654-9658.
Maassab , "Adaptation and growth characteristics of influenza virus at 25 degrees C.", Nature, vol. 213, 1967, pp. 612-614.
Maassab et al., "Biologic and immunologic characteristics of cold-adapted influenza virus", J. Immunol., vol. 102, 1969, pp. 728-732.
Margine et al., "Hemagglutinin stalk-based universal vaccine constructs protect against group 2 influenza A viruses", J. Virol, vol. 87, 2013, pp. 10435-10446.
Martinez-Sobrido et al., "Generation of recombinant influenza virus from plasmid DNA", J. Vis. Exp., vol. 42, e2057, 2010, 5 pages.

(56) References Cited

OTHER PUBLICATIONS

Meier-Ewert et al., "Time course of synthesis and assembly of influenza virus proteins", Journal of virology, vol. 14, 1974, pp. 1083-1091.

Miller et al., "Neutralizing antibodies against previously encountered influenza virus strains increase over time: a longitudinal analysis", Sci Transl. Med., vol. 5, 2013, pp. 198ra107.

Nogales et al., "Influenza A virus attenuation by codon deoptimization of the NS gene for vaccine development", J. Virol, vol. 88, 2014, pp. 10524-1 0540.

Oster et al., "Benefits and risks of live attenuated influenza vaccine in young children", Am. J. Manag. Care, vol. 16, 2010, pp. e325-e344.

Osterholm et al., "Efficacy and effectiveness of influenza vaccines: a systematic review and meta-analysis", Lancet Infect Dis, 2012, vol. 12, pp. 36-44.

PCT/US2014/047275, "International Preliminary Report on Patentability", dated Jan. 28, 2016, 8 pages.

PCT/US2014/047275, "International Search Report and Written Opinion", dated Nov. 25, 2014, 14 pages.

PCT/US2016/028992, "International Preliminary Report on Patentability", dated Nov. 2, 2017, 12 pages.

PCT/US2016/028992, "International Search Report and Written Opinion", dated Sep. 30, 2016, 20 pages.

PCT/US2016/028992, "Invitation to Pay Add'l Fees and Partial Search Report", dated Aug. 1, 2016, 7 pages.

Pflug et al., "Structure of influenza A polymerase bound to the viral RNA promoter", Nature, vol. 000, 2014, pp. 1-16.

Reed et al., "A simple method of estimating fifty per cent endpoints", Am. J. Hygiene, vol. 27, 1938, pp. 493-497.

Snyder et al., "Four viral genes independently contribute to attenuation of live influenza A/Ann Arbor/6/60 (H2N2) cold-adapted reassortant virus vaccines", Journal of virology, vol. 62, 1988, pp. 488-495.

Subbarao et al., "Characterization of an avian influenza A (H5N1) virus isolated from a child with a fatal respiratory illness", Science, vol. 279, No. 5349, Jan. 1998, pp. 393-396.

Suguitan et al., "Live, attenuated influenza A H5N1 candidate vaccines provide broad cross-protection in m

Fold discrepancy in semiinfectious particle formation at 39°C vs 33°C for the indicated viruses in MDCK cells

SEQUENCE LISTING

<160> NUMBER OF SEQ ID NOS: 13

<210> SEQ ID NO 1
<211> LENGTH: 757
<212> TYPE: PRT
<213> ORGANISM: Influenza A virus

<400> SEQUENCE: 1

Met Asp Val Asn Pro Thr Leu Leu Phe Leu Lys Val Pro Ala Gln Asn
1               5                   10                  15

```
Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
            35                  40                  45

Tyr Ser Glu Lys Gly Lys Trp Thr Thr Asn Thr Glu Thr Gly Ala His
 50                  55                  60

Gln Leu Asn Pro Ile Asp Gly Pro Leu Pro Glu Asp Asn Glu Pro Ser
 65                  70                  75                  80

Gly Tyr Ala Gln Thr Asp Cys Val Leu Glu Ala Met Ala Phe Leu Glu
                 85                  90                  95

Glu Ser His Pro Gly Ile Phe Glu Asn Ser Cys Leu Glu Thr Met Glu
                100                 105                 110

Val Ile Gln Gln Thr Arg Val Asp Lys Leu Thr Gln Gly Arg Gln Thr
            115                 120                 125

Tyr Asp Trp Thr Leu Asn Arg Asn Gln Pro Ala Ala Thr Ala Leu Ala
130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Ile Glu Ser Met Asp Lys
                165                 170                 175

Glu Glu Met Glu Ile Thr Thr His Phe Gln Arg Lys Arg Arg Val Arg
                180                 185                 190

Asp Asn Met Thr Lys Lys Met Val Thr Gln Arg Thr Ile Gly Lys Lys
            195                 200                 205

Lys Gln Arg Leu Asn Lys Arg Ser Tyr Leu Ile Arg Ala Leu Thr Leu
            210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
            275                 280                 285

Met Met Thr Asn Ser Gln Asp Thr Glu Leu Ser Phe Thr Ile Thr Gly
            290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Lys Ser Lys Ser Met Lys Leu Arg Thr Gln Ile
            355                 360                 365

Pro Ala Glu Met Leu Ala Ser Ile Asp Leu Lys Tyr Phe Asn Glu Ser
            370                 375                 380

Thr Arg Lys Lys Ile Glu Lys Ile Arg Pro Leu Leu Ile Asp Gly Thr
385                 390                 395                 400

Val Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430
```

```
Lys Thr Thr Tyr Trp Trp Asp Gly Leu Gln Ser Ser Asp Phe Ala
            435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
        530                 535                 540

Gln Leu Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
        610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Ile Leu Glu Asp Glu Gln Met
            675                 680                 685

Tyr Gln Lys Cys Cys Asn Leu Phe Glu Lys Phe Phe Pro Ser Ser Ser
        690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Ile Cys Ser Thr Ile Glu Glu
            740                 745                 750

Leu Arg Arg Gln Lys
            755

<210> SEQ ID NO 2
<211> LENGTH: 757
<212> TYPE: PRT
<213> ORGANISM: Influenza A virus

<400> SEQUENCE: 2

Met Asp Val Asn Pro Thr Leu Leu Phe Leu Lys Ile Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45
```

```
Tyr Ser Glu Lys Gly Lys Trp Thr Thr Asn Thr Glu Thr Gly Ala Pro
 50                  55                  60

Gln Leu Asn Pro Ile Asp Gly Pro Leu Pro Glu Asp Asn Glu Pro Ser
 65                  70                  75                  80

Gly Tyr Ala Gln Thr Asp Cys Val Leu Glu Ala Met Ala Phe Leu Glu
                 85                  90                  95

Glu Ser His Pro Gly Ile Phe Glu Asn Ser Cys Leu Glu Thr Met Glu
             100                 105                 110

Val Val Gln Gln Thr Arg Val Asp Lys Leu Thr Gln Gly Arg Gln Thr
         115                 120                 125

Tyr Asp Trp Thr Leu Asn Arg Asn Gln Pro Ala Ala Thr Ala Leu Ala
     130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                 165                 170                 175

Glu Glu Ile Glu Ile Thr Thr His Phe Gln Arg Lys Arg Arg Val Arg
             180                 185                 190

Asp Asn Met Thr Lys Lys Met Val Thr Gln Arg Thr Ile Gly Lys Lys
         195                 200                 205

Lys Gln Arg Leu Asn Lys Arg Gly Tyr Leu Ile Arg Ala Leu Thr Leu
     210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                 245                 250                 255

Thr Leu Ala Arg Ser Ile Cys Glu Lys Leu Glu Gln Ser Gly Leu Pro
             260                 265                 270

Val Gly Gly Asn Glu Lys Lys Ala Lys Leu Ala Asn Val Val Arg Lys
         275                 280                 285

Met Met Thr Asn Ser Gln Asp Thr Glu Ile Ser Phe Thr Ile Thr Gly
     290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Ile
                 325                 330                 335

Leu Ser Met Ala Pro Ile Met Phe Ser Asn Lys Met Ala Arg Leu Gly
             340                 345                 350

Lys Gly Tyr Met Phe Glu Ser Lys Arg Met Lys Ile Arg Thr Gln Ile
         355                 360                 365

Pro Ala Glu Met Leu Ala Ser Ile Asp Leu Lys Tyr Phe Asn Glu Ser
     370                 375                 380

Thr Lys Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                 405                 410                 415

Thr Val Leu Gly Val Ser Ile Leu Asn Leu Gly Gln Lys Lys Tyr Thr
             420                 425                 430

Lys Thr Ile Tyr Trp Trp Asp Gly Leu Gln Ser Ser Asp Asp Phe Ala
         435                 440                 445

Leu Ile Val Asn Ala Pro Asn His Glu Gly Ile Gln Ala Gly Val Asp
     450                 455                 460
```

-continued

```
Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
            485                 490                 495

Tyr Arg Tyr Gly Phe Val Ala Asn Phe Ser Met Glu Leu Pro Ser Phe
        500                 505                 510

Gly Val Ser Gly Val Asn Glu Ser Ala Asp Met Ser Ile Gly Val Thr
    515                 520                 525

Val Ile Lys Asn Asn Met Ile Asn Asn Asp Leu Gly Pro Ala Thr Ala
530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Lys Val Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Asp Asp Tyr Arg Gly Arg Leu
    610                 615                 620

Cys Asn Pro Leu Asn Pro Phe Val Ser His Lys Glu Ile Asp Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Val Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys
        755

<210> SEQ ID NO 3
<211> LENGTH: 757
<212> TYPE: PRT
<213> ORGANISM: Influenza A virus

<400> SEQUENCE: 3

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Arg Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80
```

-continued

```
Gly Tyr Ala Gln Thr Asp Cys Val Leu Glu Ala Met Ala Phe Leu Glu
                85                  90                  95
Glu Ser His Pro Gly Ile Phe Glu Asn Ser Cys Leu Glu Thr Met Glu
            100                 105                 110
Ala Val Gln Gln Thr Arg Val Asp Lys Leu Thr Gln Gly Arg Gln Thr
        115                 120                 125
Tyr Asp Trp Thr Leu Asn Arg Asn Gln Pro Ala Ala Thr Ala Leu Ala
    130                 135                 140
Asn Thr Ile Glu Val Phe Arg Ser Asn Gly Leu Thr Ala Asn Glu Ser
145                 150                 155                 160
Gly Arg Leu Ile Asp Phe Leu Lys Asp Val Met Glu Ser Met Asp Lys
                165                 170                 175
Glu Glu Met Glu Ile Thr Thr His Phe Gln Arg Lys Arg Arg Val Arg
            180                 185                 190
Asp Asn Met Thr Lys Lys Met Val Thr Gln Arg Thr Ile Gly Lys Lys
        195                 200                 205
Lys Gln Arg Val Asn Lys Arg Gly Tyr Leu Ile Arg Ala Leu Thr Leu
    210                 215                 220
Asn Thr Met Thr Lys Asp Ala Glu Arg Gly Lys Leu Lys Arg Arg Ala
225                 230                 235                 240
Ile Ala Thr Pro Gly Met Gln Ile Arg Gly Phe Val Tyr Phe Val Glu
                245                 250                 255
Thr Leu Ala Arg Ser Ile Cys Glu Lys Leu Glu Gln Ser Gly Leu Pro
            260                 265                 270
Val Gly Gly Asn Glu Lys Lys Ala Lys Leu Ala Asn Val Val Arg Lys
        275                 280                 285
Met Met Thr Asn Ser Gln Asp Thr Glu Leu Ser Phe Thr Ile Thr Gly
    290                 295                 300
Asp Asn Thr Lys Trp Asn Glu Asn Gln Asn Pro Arg Met Phe Leu Ala
305                 310                 315                 320
Met Ile Thr Tyr Ile Thr Lys Asn Gln Pro Glu Trp Phe Arg Asn Ile
                325                 330                 335
Leu Ser Ile Ala Pro Ile Met Phe Ser Asn Lys Met Ala Arg Leu Gly
            340                 345                 350
Lys Gly Tyr Met Phe Glu Ser Lys Lys Met Lys Leu Arg Thr Gln Ile
        355                 360                 365
Pro Ala Glu Met Leu Ala Ser Ile Asp Leu Lys Tyr Phe Asn Glu Ser
    370                 375                 380
Thr Arg Lys Lys Ile Glu Lys Ile Arg Pro Leu Leu Ile Asp Gly Thr
385                 390                 395                 400
Ala Ser Leu Ser Pro Gly Met Met Met Gly Met Phe Asn Met Leu Ser
                405                 410                 415
Thr Val Leu Gly Val Ser Ile Leu Asn Leu Gly Gln Lys Lys Tyr Thr
            420                 425                 430
Lys Thr Thr Tyr Trp Trp Asp Gly Leu Gln Ser Ser Asp Asp Phe Ala
        435                 440                 445
Leu Ile Val Asn Ala Pro Asn His Glu Gly Ile Gln Ala Gly Val Asp
    450                 455                 460
Arg Phe Tyr Arg Thr Cys Lys Leu Val Gly Ile Asn Met Ser Lys Lys
465                 470                 475                 480
Lys Ser Tyr Ile Asn Lys Thr Gly Thr Phe Glu Phe Thr Ser Phe Phe
                485                 490                 495
```

```
Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
            530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
            565                 570                 575

Lys Lys Leu Trp Asp Gln Thr Gln Ser Arg Ala Gly Leu Leu Val Ser
            580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asn Tyr Arg Gly Arg Leu
            610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
            645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
            675                 680                 685

Tyr Gln Lys Cys Cys Asn Leu Phe Glu Lys Phe Phe Pro Ser Ser Ser
690                 695                 700

Tyr Arg Arg Pro Ile Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
            725                 730                 735

Lys Glu Glu Phe Ser Glu Ile Met Arg Ile Cys Ser Thr Ile Glu Glu
            740                 745                 750

Leu Arg Arg Gln Lys
            755

<210> SEQ ID NO 4
<211> LENGTH: 744
<212> TYPE: PRT
<213> ORGANISM: Influenza A virus

<400> SEQUENCE: 4

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
            35                  40                  45

Tyr Ser Glu Lys Gly Arg Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Leu Phe Glu Asn Ser Cys Leu Glu Thr Met Glu
            100                 105                 110
```

Val Val Gln Gln Thr Arg Val Asp Lys Leu Thr Gln Gly Arg Gln Thr
            115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
                180                 185                 190

Asp Asn Met Thr Lys Lys Met Val Thr Gln Arg Thr Ile Gly Lys Lys
                195                 200                 205

Lys Gln Lys Leu Thr Lys Lys Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val His Phe Val Glu
                245                 250                 255

Ala Leu Ala Arg Ser Ile Cys Glu Lys Leu Glu Gln Ser Gly Leu Pro
                260                 265                 270

Val Gly Gly Asn Glu Lys Lys Ala Lys Leu Ala Asn Val Val Arg Lys
            275                 280                 285

Met Met Thr Asn Ser Gln Asp Thr Glu Leu Ser Phe Thr Val Thr Gly
            290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
                340                 345                 350

Lys Gly Tyr Met Phe Glu Ser Lys Ser Met Lys Leu Arg Thr Gln Ile
            355                 360                 365

Pro Ala Glu Met Leu Ala Asn Ile Asp Leu Lys Tyr Phe Asn Glu Ser
    370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Gly Met Phe Asn Met Leu Ser
            405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
    435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
            515                 520                 525

-continued

```
Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Gly Leu Lys Trp Glu Leu Met Asp Glu Asp Tyr Gln Gly Arg Leu
    610                 615                 620

Cys Asn Pro Leu Asn Pro Phe Val Ser His Lys Glu Val Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Thr Leu Phe Glu Lys Phe Phe Pro Ser Ser Ser
    690                 695                 700

Tyr Arg Arg Pro Val Gly Ile Ser Ser Met Met Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Leu
            740
```

<210> SEQ ID NO 5
<211> LENGTH: 2274
<212> TYPE: DNA
<213> ORGANISM: Influenza A virus

<400> SEQUENCE: 5

```
atggatgtca atccgacctt acttttcttg aaagttccag cgcaaaatgc cataagtact      60
acattccctt atactggaga tcctccatac agccatggaa caggaacagg atacaccatg     120
gacacagtca acagaacaca tcaatattca gaaaagggga agtggacaac aaacacggaa     180
actggagcgc accaacttaa cccaattgat ggaccactac ctgaggacaa tgaaccaagt     240
ggatatgcac aaacagactg cgtcctggaa gcaatggctt tccttgaaga atcccaccca     300
ggaatctttg aaaactcgtg tcttgaaacg atggaagtta ttcaacaaac aagagtggac     360
aaactgaccc aaggtcgtca gacctatgat tggacattga acagaaatca gccggctgca     420
actgcgctag ccaacactat agaggtcttc agatcgaatg gcctgacagc taatgaatcg     480
ggaaggctaa tagatttcct caaggatgtg atagaatcaa tggataaaga ggagatggaa     540
atcacaacac acttccaaag aaaaagaaga gtaagagaca acatgaccaa gaaaatggtc     600
acacaacgaa caataggaaa gaagaagcaa agattgaaca agagaagcta tctaataaga     660
gcactgacat tgaacacaat gactaaagat gcagagagag gtaaattaaa gagaagagca     720
attgcaacac ccggtatgca gatcagaggg ttcgtgtact ttgtcgaaac actagcgaga     780
agtatttgtg agaagcttga acagtctggg cttccggttg gaggtaatga aaagaaggct     840
aaactggcaa atgttgtgcg aaaaatgatg actaattcac aagacacaga gctctctttc     900
```

```
acaattactg agacaatac caaatggaat gagaatcaaa atcctcggat gttcctggcg      960
atgataacat acatcacaag aaatcaacct gaatggttta gaaacgtcct gagcatcgca   1020
cctataatgt tctcaaataa aatggcaaga ctagggaaag gatacatgtt caaaagcaag   1080
agcatgaagc tccgaacaca aataccagca gaaatgctag caagtattga cctgaaatac   1140
tttaatgaat caacaagaaa gaaaatcgag aaaataaggc ctctcctaat agatggcaca   1200
gtctcattga gtcctggaat gatgatgggc atgttcaaca tgctaagtac agtcttagga   1260
gtctcaatcc tgaatcttgg acaaaagaag tacaccaaaa caacatactg gtgggacgga   1320
ctccaatcct ctgatgactt cgccctcata gtgaatgcac caaatcatga gggaatacaa   1380
gcagggtgg atagattcta cagaacctgc aagctagtcg aatcaatat gagcaaaaag   1440
aagtcctaca taaataggac agggacattt gaattcacaa gcttttttcta tcgctatgga   1500
tttgtagcca attttagcat ggagctgccc agctttggag tgtctggaat taatgaatcg   1560
gctgatatga gcattggggt aacagtgata agaacaaca tgataaacaa tgaccttggg   1620
ccagcaacag cccaactggc tcttcaacta ttcatcaaag actacagata tacgtaccgg   1680
tgccacagag gagacacaca aattcagaca aggagatcat tcgagctaaa gaagctgtgg   1740
gagcaaaccc gctcaaaggc aggacttttg gtttcggatg gaggaccaaa cttatacaat   1800
atccggaatc tccacattcc agaagtctgc ttgaagtggg agctaatgga tgaagactat   1860
caggggaggc tttgtaatcc cctgaatcca tttgtcagtc ataaggagat tgagtctgta   1920
aacaatgctg tggtaatgcc agctcacggt ccagccaaga gcatggaata tgatgctgtt   1980
gctactacac actcctggat ccctaagagg aaccgctcca ttctcaacac aagccaaagg   2040
ggaattcttg aagatgaaca gatgtatcag aagtgttgca atctattcga gaaattcttc   2100
cctagcagtt cgtacaggag accagttgga atttccagca tggtggaggc catggtgtct   2160
agggcccgga ttgatgcacg gattgacttc gagtctggac ggattaagaa agaggagttc   2220
gctgagatca tgaagatctg ttccaccatt gaagagctca gacggcaaaa atag         2274
```

<210> SEQ ID NO 6
<211> LENGTH: 759
<212> TYPE: PRT
<213> ORGANISM: Influenza A virus

<400> SEQUENCE: 6

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Ser Asp Ala Gly Ser Asp Arg Val Met Val Ser Pro Leu Ala Val
                85                  90                  95

Thr Trp Trp Asn Arg Asn Gly Pro Met Thr Ser Thr Val His Tyr Pro
            100                 105                 110

Lys Ile Tyr Lys Thr Tyr Phe Glu Lys Val Glu Arg Leu Lys His Gly
        115                 120                 125

-continued

```
Thr Phe Gly Pro Val His Phe Arg Asn Gln Val Lys Ile Arg Arg
    130                 135                 140
Val Asp Ile Asn Pro Gly His Ala Asp Leu Ser Ala Lys Glu Ala Gln
145                 150                 155                 160
Asp Val Ile Met Glu Val Val Phe Pro Asn Glu Val Gly Ala Arg Ile
                165                 170                 175
Leu Thr Ser Glu Ser Gln Leu Thr Ile Thr Lys Glu Lys Lys Glu Glu
            180                 185                 190
Leu Gln Asp Cys Lys Ile Ser Pro Leu Met Val Ala Tyr Met Leu Glu
        195                 200                 205
Arg Glu Leu Val Arg Lys Thr Arg Phe Leu Pro Val Ala Gly Gly Thr
    210                 215                 220
Ser Ser Val Tyr Ile Glu Val Leu His Leu Thr Gln Gly Thr Cys Trp
225                 230                 235                 240
Glu Gln Met Tyr Thr Pro Gly Gly Glu Val Arg Asn Asp Asp Val Asp
                245                 250                 255
Gln Ser Leu Ile Ile Ala Ala Arg Asn Ile Val Arg Arg Ala Ala Val
            260                 265                 270
Ser Ala Asp Pro Leu Ala Ser Leu Leu Glu Met Cys His Ser Thr Gln
        275                 280                 285
Ile Gly Gly Thr Arg Met Val Asp Ile Leu Arg Gln Asn Pro Thr Glu
    290                 295                 300
Glu Gln Ala Val Glu Ile Cys Lys Ala Ala Met Gly Leu Arg Ile Ser
305                 310                 315                 320
Ser Ser Phe Ser Phe Gly Gly Phe Thr Phe Lys Arg Thr Ser Gly Ser
                325                 330                 335
Ser Val Lys Arg Glu Glu Glu Val Leu Thr Gly Asn Leu Gln Thr Leu
            340                 345                 350
Lys Ile Arg Val His Glu Gly Tyr Glu Glu Phe Thr Met Val Gly Lys
        355                 360                 365
Arg Ala Thr Ala Ile Leu Arg Lys Ala Thr Arg Arg Leu Ile Gln Leu
    370                 375                 380
Ile Val Ser Gly Arg Asp Glu Gln Ser Ile Ala Glu Ala Ile Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
            420                 425                 430
Gln Leu Leu Arg His Phe Gln Lys Asp Ala Lys Val Leu Phe Gln Asn
        435                 440                 445
Trp Gly Ile Glu His Ile Asp Asn Val Met Gly Met Ile Gly Val Leu
    450                 455                 460
Pro Asp Met Thr Pro Ser Thr Glu Met Ser Met Arg Gly Val Arg Val
465                 470                 475                 480
Ser Lys Met Gly Val Asp Glu Tyr Ser Ser Ala Glu Arg Val Val Val
                485                 490                 495
Ser Ile Asp Arg Phe Leu Arg Val Arg Asp Gln Arg Gly Asn Val Leu
            500                 505                 510
Leu Ser Pro Glu Glu Val Ser Glu Thr Gln Gly Thr Glu Lys Leu Thr
        515                 520                 525
Ile Thr Tyr Ser Ser Ser Met Met Trp Glu Ile Asn Gly Pro Glu Ser
    530                 535                 540
Val Leu Val Asn Thr Tyr Gln Trp Ile Ile Arg Asn Trp Glu Thr Val
```

-continued

```
                545                 550                 555                 560
            Lys Ile Gln Trp Ser Gln Asn Pro Thr Met Leu Tyr Asn Lys Met Glu
                            565                 570                 575
            Phe Glu Pro Phe Gln Ser Leu Val Pro Lys Ala Ile Arg Gly Gln Tyr
                        580                 585                 590
            Ser Gly Phe Val Arg Thr Leu Phe Gln Gln Met Arg Asp Val Leu Gly
                    595                 600                 605
            Thr Phe Asp Thr Thr Gln Ile Ile Lys Leu Leu Pro Phe Ala Ala Ala
                610                 615                 620
            Pro Pro Lys Gln Ser Arg Met Gln Phe Ser Ser Leu Thr Val Asn Val
            625                 630                 635                 640
            Arg Gly Ser Gly Met Arg Ile Leu Val Arg Gly Asn Ser Pro Ile Phe
                            645                 650                 655
            Asn Tyr Asn Lys Thr Thr Lys Arg Leu Thr Ile Leu Gly Lys Asp Ala
                        660                 665                 670
            Gly Thr Leu Thr Glu Asp Pro Asp Glu Gly Thr Ser Gly Val Glu Ser
                    675                 680                 685
            Ala Val Leu Arg Gly Phe Leu Ile Leu Gly Lys Glu Asp Arg Arg Tyr
                690                 695                 700
            Gly Pro Ala Leu Ser Ile Asn Glu Leu Ser Asn Leu Ala Lys Gly Glu
            705                 710                 715                 720
            Lys Ala Asn Val Leu Ile Gly Gln Gly Asp Val Val Leu Val Met Lys
                            725                 730                 735
            Arg Lys Arg Asn Ser Ser Ile Leu Thr Asp Ser Gln Thr Ala Thr Lys
                        740                 745                 750
            Arg Ile Arg Met Ala Ile Asn
                    755

<210> SEQ ID NO 7
<211> LENGTH: 751
<212> TYPE: PRT
<213> ORGANISM: Influenza A virus

<400> SEQUENCE: 7

Ile Lys Glu Leu Trp Asp Leu Met Ser Gln Ser Arg Thr Arg Glu Ile
            1               5                   10                  15
            Leu Thr Lys Thr Thr Val Asp His Met Ala Ile Ile Lys Lys Tyr Thr
                            20                  25                  30
            Ser Gly Arg Gln Glu Lys Asn Pro Ala Leu Arg Met Lys Trp Met Met
                        35                  40                  45
            Ala Met Lys Tyr Pro Ile Thr Ala Asp Lys Arg Ile Met Glu Met Ile
                    50                  55                  60
            Pro Glu Arg Asn Glu Gln Gly Gln Thr Leu Trp Ser Lys Thr Asn Asp
            65                  70                  75                  80
            Ala Gly Ser Asp Arg Val Met Glu Ser Pro Leu Ala Val Thr Trp Trp
                            85                  90                  95
            Asn Arg Asn Gly Pro Thr Thr Ser Thr Val His Tyr Pro Lys Val Tyr
                        100                 105                 110
            Lys Thr Tyr Phe Glu Lys Val Glu Arg Leu Lys His Gly Thr Phe Gly
                    115                 120                 125
            Pro Val His Phe Arg Asn Gln Val Lys Ile Arg Arg Arg Val Asp Met
                130                 135                 140
            Asn Pro Gly His Ala Asp Leu Ser Ala Lys Glu Ala Gln Asp Val Ile
            145                 150                 155                 160
```

-continued

```
Met Glu Val Val Phe Pro Asn Glu Val Gly Ala Arg Ile Leu Thr Ser
                165                 170                 175
Glu Ser Gln Leu Thr Ile Thr Lys Glu Lys Arg Glu Leu Lys Asn
        180                 185                 190
Cys Asn Ile Ala Pro Leu Met Val Ala Tyr Met Leu Glu Arg Glu Leu
        195                 200                 205
Val Arg Lys Thr Arg Phe Leu Pro Val Ala Gly Gly Thr Ser Ser Val
        210                 215                 220
Tyr Ile Glu Val Leu His Leu Thr Gln Gly Thr Cys Trp Glu Gln Met
225                 230                 235                 240
Tyr Thr Pro Gly Gly Glu Val Arg Asn Asp Asp Val Asp Gln Ser Leu
                245                 250                 255
Ile Ile Ala Val Gly Asn Ile Val Arg Arg Ala Thr Val Ser Ala Asp
                260                 265                 270
Pro Leu Ala Ser Leu Leu Glu Met Cys His Ser Thr Gln Ile Gly Gly
        275                 280                 285
Val Arg Met Val Asp Ile Leu Lys Gln Asn Pro Thr Glu Glu Gln Ala
        290                 295                 300
Val Asp Ile Cys Lys Ala Ala Met Gly Leu Lys Ile Ser Ser Ser Phe
305                 310                 315                 320
Ser Phe Gly Gly Phe Thr Phe Lys Arg Thr Lys Gly Ser Ser Val Lys
                325                 330                 335
Arg Glu Glu Glu Val Leu Thr Gly Asn Leu Gln Thr Leu Lys Ile Lys
                340                 345                 350
Val His Glu Gly Tyr Glu Glu Phe Thr Met Val Gly Arg Arg Ala Thr
        355                 360                 365
Ala Ile Leu Arg Lys Ala Thr Arg Arg Met Ile Gln Leu Ile Val Ser
        370                 375                 380
Gly Arg Asp Glu Gln Ser Ile Ala Glu Ala Ile Ile Val Ala Met Val
385                 390                 395                 400
Phe Ser Gln Glu Asp Cys Met Ile Lys Ala Val Arg Gly Asp Leu Asn
                405                 410                 415
Phe Val Asn Arg Ala Asn Gln Arg Leu Asn Pro Met His Gln Leu Leu
        420                 425                 430
Arg His Phe Gln Lys Asp Ala Lys Val Leu Phe Gln Asn Trp Gly Thr
        435                 440                 445
Glu Pro Ile Asp Asn Val Met Gly Met Ile Gly Ile Leu Pro Asp Met
        450                 455                 460
Thr Pro Ser Thr Glu Met Ser Leu Arg Gly Val Arg Val Ser Lys Met
465                 470                 475                 480
Gly Val Asp Glu Tyr Ser Ser Thr Glu Arg Val Val Val Ser Ile Asp
                485                 490                 495
Arg Phe Leu Arg Val Arg Asp Gln Arg Gly Asn Val Leu Leu Ser Pro
                500                 505                 510
Glu Glu Val Ser Glu Thr Gln Gly Met Glu Lys Leu Thr Ile Thr Tyr
        515                 520                 525
Ser Ser Ser Met Met Trp Glu Ile Asn Gly Pro Glu Ser Val Leu Val
        530                 535                 540
Asn Thr Tyr Gln Trp Ile Ile Arg Asn Trp Glu Thr Val Lys Ile Gln
545                 550                 555                 560
Trp Ser Gln Glu Pro Thr Met Leu Tyr Asn Lys Met Glu Phe Glu Pro
                565                 570                 575
Phe Gln Ser Leu Val Pro Lys Ala Ala Arg Ser Gln Tyr Ser Gly Phe
```

```
                580             585             590
Val Arg Thr Leu Phe Gln Gln Met Arg Asp Val Leu Gly Thr Phe Asp
            595             600             605

Thr Val Gln Ile Ile Lys Leu Leu Pro Phe Ala Ala Ala Pro Pro Glu
610             615             620

Gln Ser Arg Met Gln Phe Ser Ser Leu Thr Val Asn Val Arg Gly Ser
625             630             635             640

Gly Met Arg Ile Leu Val Arg Gly Asn Ser Pro Ala Phe Asn Tyr Asn
            645             650             655

Lys Thr Thr Lys Arg Leu Thr Ile Leu Gly Lys Asp Ala Gly Ala Leu
            660             665             670

Thr Glu Asp Pro Asp Glu Gly Thr Ala Gly Val Glu Ser Ala Val Leu
            675             680             685

Arg Gly Phe Leu Ile Leu Gly Lys Glu Asp Lys Arg Tyr Gly Pro Ala
            690             695             700

Leu Ser Ile Asn Glu Leu Ser Asn Leu Thr Lys Gly Glu Lys Ala Asn
705             710             715             720

Val Leu Ile Gly Gln Gly Asp Val Val Leu Val Met Lys Arg Lys Arg
            725             730             735

Asp Ser Ser Ile Leu Thr Asp Ser Gln Thr Ala Thr Lys Arg Ile
            740             745             750
```

<210> SEQ ID NO 8
<211> LENGTH: 759
<212> TYPE: PRT
<213> ORGANISM: Influenza A virus

<400> SEQUENCE: 8

```
Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Val His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205
```

```
Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Val Arg Asn Asp Asp Val Asp
                245                 250                 255

Gln Ser Leu Ile Ile Ala Ala Arg Asn Ile Val Arg Arg Ala Thr Val
        260                 265                 270

Ser Ala Asp Pro Leu Ala Ser Leu Glu Met Cys His Ser Thr Gln
        275                 280                 285

Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Val Leu Thr Gly Asn Leu Gln Thr Leu
        340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Leu Ile Gln Leu
370                 375                 380

Ile Val Ser Gly Lys Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
                420                 425                 430

Gln Leu Leu Arg His Phe Gln Lys Asp Ala Lys Val Leu Phe Gln Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Asn Val
545                 550                 555                 560

Lys Ile Gln Trp Ser Gln Asp Pro Thr Met Leu Tyr Asn Lys Met Glu
                565                 570                 575

Phe Glu Pro Phe Gln Ser Leu Val Pro Lys Ala Ala Arg Gly Gln Tyr
                580                 585                 590

Ser Gly Phe Val Arg Val Leu Phe Gln Gln Met Arg Asp Val Leu Gly
        595                 600                 605

Thr Phe Asp Thr Val Gln Ile Ile Lys Leu Leu Pro Phe Ala Ala Ala
    610                 615                 620

Pro Pro Lys Gln Ser Arg Met Gln Phe Ser Ser Leu Thr Val Asn Val
```

```
                625                 630                 635                 640
Arg Gly Ser Gly Met Arg Ile Val Val Arg Gly Asn Ser Pro Val Phe
                        645                 650                 655
Asn Tyr Asn Lys Ala Thr Lys Arg Leu Thr Val Leu Gly Lys Asp Ala
                660                 665                 670
Gly Ala Leu Met Glu Asp Pro Asp Glu Gly Thr Ala Gly Val Glu Ser
                675                 680                 685
Ala Val Leu Arg Gly Phe Leu Ile Leu Gly Lys Glu Asp Lys Arg Tyr
        690                 695                 700
Gly Pro Ala Leu Ser Ile Asn Glu Leu Ser Asn Leu Ala Lys Gly Glu
705                 710                 715                 720
Lys Ala Asn Val Leu Ile Gly Gln Gly Asp Val Val Leu Val Met Lys
                    725                 730                 735
Arg Lys Arg Asp Ser Ser Ile Leu Thr Asp Ser Gln Thr Ala Thr Lys
                740                 745                 750
Arg Ile Arg Met Ala Ile Asn
        755
```

<210> SEQ ID NO 9
<211> LENGTH: 179
<212> TYPE: PRT
<213> ORGANISM: Influenza A virus

<400> SEQUENCE: 9

```
Ser Arg Thr Arg Glu Ile Leu Thr Lys Thr Thr Val Asp His Met Ala
1               5                   10                  15
Ile Ile Lys Lys Tyr Thr Ser Gly Arg Gln Glu Lys Asn Pro Ser Leu
                20                  25                  30
Arg Met Lys Trp Met Met Ala Met Lys Tyr Pro Ile Thr Ala Asp Lys
            35                  40                  45
Arg Ile Met Glu Met Ile Pro Glu Arg Asn Glu Gln Gly Gln Thr Leu
        50                  55                  60
Trp Ser Lys Thr Asn Asp Ala Gly Ser Asn Arg Val Met Val Ser Pro
65                  70                  75                  80
Leu Ala Val Thr Trp Trp Asn Arg Asn Gly Pro Thr Thr Ser Thr Ile
                    85                  90                  95
His Tyr Pro Lys Val Tyr Lys Thr Tyr Phe Glu Lys Val Glu Arg Leu
                100                 105                 110
Lys His Gly Thr Phe Gly Pro Val His Phe Arg Asn Gln Val Lys Ile
            115                 120                 125
Arg Arg Arg Val Asp Val Asn Pro Gly His Ala Asp Leu Ser Ala Lys
        130                 135                 140
Glu Ala Gln Asp Val Ile Met Glu Val Val Phe Pro Asn Glu Val Gly
145                 150                 155                 160
Ala Arg Ile Leu Thr Ser Glu Ser Gln Leu Ala Ile Thr Lys Glu Lys
                    165                 170                 175
Lys Glu Glu
```

<210> SEQ ID NO 10
<211> LENGTH: 716
<212> TYPE: PRT
<213> ORGANISM: Inlfluenza A virus

<400> SEQUENCE: 10

```
Met Glu Asp Phe Val Arg Gln Cys Phe Asn Pro Met Ile Val Glu Leu
1               5                   10                  15
```

```
Ala Glu Lys Thr Met Lys Glu Tyr Gly Glu Asp Leu Lys Ile Glu Thr
             20                  25                  30

Asn Lys Phe Ala Ala Ile Cys Thr His Leu Glu Val Cys Phe Met Tyr
         35                  40                  45

Ser Asp Phe His Phe Ile Asn Glu Gln Gly Ser Ile Ile Val Glu
 50                  55                  60

Leu Gly Asp Pro Asn Ala Leu Leu Lys His Arg Phe Glu Ile Ile Glu
 65                  70                  75                  80

Gly Arg Asp Arg Thr Met Ala Trp Thr Val Val Asn Ser Ile Cys Asn
                 85                  90                  95

Thr Thr Gly Ala Glu Lys Pro Lys Phe Leu Pro Asp Leu Tyr Asp Tyr
             100                 105                 110

Lys Glu Asn Arg Phe Ile Glu Ile Gly Val Thr Arg Arg Glu Val His
         115                 120                 125

Ile Tyr Tyr Leu Glu Lys Ala Asn Lys Ile Lys Ser Glu Lys Thr His
 130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430
```

```
Ala Pro Ile Glu His Ile Ala Ser Met Arg Arg Asn Tyr Phe Thr Ser
            435                 440                 445

Glu Val Ser His Cys Arg Ala Thr Glu Tyr Ile Met Lys Gly Val Tyr
        450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Lys Gly Arg Ser His Leu Arg
            500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
        530                 535                 540

Ile Gly Asp Met Leu Ile Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
            610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
        690                 695                 700

Ser Trp Phe Asn Ser Phe Leu Thr His Ala Leu Ser
705                 710                 715
```

<210> SEQ ID NO 11
<211> LENGTH: 12
<212> TYPE: DNA
<213> ORGANISM: Artificial sequence
<220> FEATURE:
<223> OTHER INFORMATION: TTTTTGGCCATG

<400> SEQUENCE: 11
tttttggcca tg                                                        12

<210> SEQ ID NO 12
<211> LENGTH: 13
<212> TYPE: DNA
<213> ORGANISM: Artificial sequence
<220> FEATURE:
<223> OTHER INFORMATION: Synthetic construct

<400> SEQUENCE: 12
tttcaggcca tga                                                       13

```
<210> SEQ ID NO 13
<211> LENGTH: 12
<212> TYPE: DNA
<213> ORGANISM: Artificial sequence
<220> FEATURE:
<223> OTHER INFORMATION: Synthetic construct

<400> SEQUENCE: 13
tttcaggcca tg                                                          12
```

ATTENUATED INFLUENZA VACCINES AND USES THEREOF

This application claims the benefit of U.S. Provisional Application No. 62/152,276 filed Apr. 24, 2015, which is hereby incorporated by reference herein in its entirety.

STATEMENT REGARDING FEDERALLY FUNDED RESEARCH

This invention was made with government support under grant number HHSN266200700008C awarded by the National Institutes of Health. The government has certain rights in the invention.

BACKGROUND

Influenza is a serious public health issue marked by mild to serious illness and, in some cases, even death. Current live attenuated influenza vaccines (LAIV) are not sufficiently attenuated for administration to children under the age of 2, pregnant women, persons with compromised immunity, or persons at high risk for complications from influenza. However, these groups of people are at high risk for complications from influenza.

SUMMARY

Provided herein is a modified influenza A virus comprising a PB1 polymerase having one or more mutations selected from the group consisting of a leucine to glutamic acid, aspartic acid or asparagine substitution at position 319 (L319E/D/N); a threonine to glutamic acid, aspartic acid, glutamine or asparagine substitution at position 323 (T323E/D/Q/N); a serine to glutamic acid, aspartic acid, glutamine or asparagine substitution at position 338 (S338E/D/Q/N); and an isoleucine to glutamic acid, aspartic acid, glutamine or asparagine substitution at position 342 (I342E/D/Q/N). Further provided is a recombinant nucleic acid encoding a PB1 polymerase of an influenza A virus, wherein the nucleic acid encodes a PB1 polymerase having one or more mutations selected from the group consisting of a leucine to glutamic acid, aspartic acid or asparagine substitution at position 319 (L319E/D/N); a threonine to glutamic acid, aspartic acid, glutamine or asparagine substitution at position 323 (T323E/D/Q/N); a serine to glutamic acid, aspartic acid, glutamine or asparagine substitution at position 338 (S338E/D/QN); and an isoleucine to glutamic acid, aspartic acid, glutamine or asparagine substitution at position 342 (I342E/D/Q/N). Also provided are populations of cells comprising any of the influenza A viruses described herein or comprising any of the nucleic acids that encode the PB1 polymerases described herein. The polymerase mutation(s) results in a temperature sensitive virus, wherein the virus has reduced growth from about 37° C. to about 39° C. (i.e., at body temperature). This reduced growth potential is advantageous for improving the safety of the virus when used to induce an immune response in a mammalian subject.

Further provided is a method for eliciting an immune response against an influenza virus in a subject, comprising administering an effective dose of a modified influenza A virus described herein in a pharmaceutically acceptable carrier.

Also provided is a method for treating or reducing the risk of an influenza infection in a subject, comprising administering to a subject with an influenza infection or at risk of exposure to an influenza infection an effective dose of a modified influenza A virus described herein, and a pharmaceutically acceptable carrier.

Also provided is a method of producing an influenza A virus described herein, comprising transfecting a population of host cells with one or more vectors. The vectors comprise nucleic acid sequences encoding the internal genome segments of an influenza A virus and a nucleic acid encoding a PB1 polymerase having one or more mutations selected from the group consisting of a leucine to glutamic acid, aspartic acid or asparagine substitution at position 319 (L319E/D/N); a threonine to glutamic acid, aspartic acid, glutamine or asparagine substitution at position 323 (T323E/D/Q/N); a serine to glutamic acid, aspartic acid, glutamine or asparagine substitution at position 338 (S338E/D/Q/N); and an isoleucine to glutamic acid, aspartic acid, glutamine or asparagine substitution at position 342 (I342E/D/Q/N). The transfected cells are cultured. The modified influenza A virus is recovered from the transfected cells.

Further provided is a method for producing an influenza immunogen comprising infecting a population of cells with any of the influenza A viruses described herein, culturing the cells, harvesting the virus from the culture and preparing an immunogen with the harvested virus.

DESCRIPTION OF THE DRAWINGS

FIG. 11 also shows that a L319N mutation at PB1 results in a PB1 polymerase with a 5-fold decrease in activity at 37° C. as compared to activity at 33° C.

FIG. 12 shows that an influenza virus with a L319Q mutation in PB1 synergizes with a N265S mutation in PB2 and results in increased safety.

DETAILED DESCRIPTION

Figure 1:
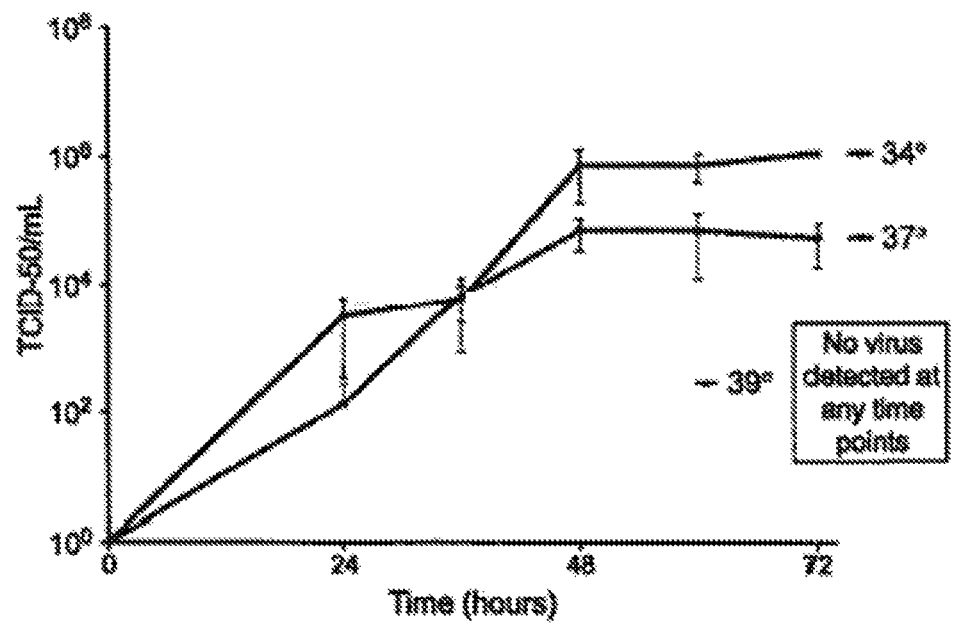
FIG. 1 shows the identification of a PB2 single gene replacement virus with temperature sensitivity at 37° C. MDCK cells were infected at a Multiplicity of Infection (MOI) of 0.01 for 1 h with a single gene replacement virus with PB2 from the cold passaged A/AnnArbor/6/60, and all other genes from a seasonal strain A/Korea/82. Cells were washed once with Dulbecco's phosphate-buffered saline (PBS) with magnesium and calcium (Invitrogen), and then cultured at 34°, 37° or 39° C. in DMEM containing 0.15% bovine serum albumin (BSA) and tosylsulfonylphenylalanyl chloromethyl ketone (TPCK)-trypsin at 1 µg/ml. At the indicated time points, 10% of the culture supernatant was harvested and replaced, and viral titers were determined through TCID-50 measurements.

The current live attenuated influenza vaccine (LAIV) is recommended as the primary vaccination strategy for healthy subjects aged 2 to 49 years, because of its greater efficacy and ease-of-use than the traditional inactivated influenza vaccine in this age group. However, the current LAIV is not recommended for pregnant women, children under 2, persons with a compromised immune system, (for example, persons with HIV/AIDS), or persons at high risk for complications from influenza. Provided herein are modified, temperature sensitive influenza A viruses that have reduced growth potential. The reduced growth potential is advantageous for improving the safety of the virus when used to induce an immune response in a mammal.

Provided herein is a modified influenza A virus comprising a PB1 polymerase having one or more mutations selected from the group consisting of a mutation at position 319, a mutation at position 323, a mutation at position 338, and a mutation at position 342. Provided herein is a modified influenza A virus comprising a PB1 polymerase having one or more mutations selected from the group consisting of a leucine to glutamic acid, aspartic acid or asparagine substitution at position 319 (L319E/D/N); a threonine to glutamic acid, aspartic acid, glutamine or asparagine substitution at position 323 (T323E/D/Q/N); a serine to glutamic acid, aspartic acid, glutamine or asparagine substitution at position 338 (S338E/D/Q/N); and an isoleucine to glutamic acid, aspartic acid, glutamine or asparagine substitution at position 342 (I342E/D/Q/N).

Also provided herein is a modified influenza A virus comprising a PB1 polymerase having a L319Q mutation and one or more mutations selected from the group consisting of a threonine to glutamic acid, aspartic acid, glutamine or asparagine substitution at position 323 (T323E/D/Q/N); a serine to glutamic acid, aspartic acid, glutamine or asparagine substitution at position 338 (S338E/D/Q/N) and an isoleucine to glutamic acid, aspartic acid, glutamine or asparagine substitution at position 342 (I342E/D/Q/N).

Further provided is a modified influenza A virus comprising a PB1 polymerase having one or more mutations selected from the group consisting of a leucine to glutamic acid, aspartic acid, glutamine or asparagine substitution at position 319 (L319E/D/Q/N); a threonine to glutamic acid, aspartic acid, glutamine or asparagine substitution at position 323 (T323E/D/Q/N); a serine to glutamic acid, aspartic acid, glutamine or asparagine substitution at position 338 (S338E/D/Q/N); and an isoleucine to glutamic acid, aspartic acid, glutamine or asparagine substitution at position 342 (I342E/D/Q/N); and a PA endonuclease comprising one or more mutations in amino acids 210-237. For example, the one or more mutations in amino acids 210-237 of PA can be selected from the group consisting of a substitution at position I207, a substitution at position A215, a substitution at position S218, a substitution at position L219, a substitution at position L226, a substitution at position F229, and a substitution at position R230. One or more of the amino acids at position 207, 215, 218, 219, 226, 229 or 230 can be substituted with glutamic acid, aspartic acid, glutamine or asparagine. An example of an amino acid sequence of PA endonuclease is set forth herein as SEQ ID NO: 10 (PA endonuclease from A/Puerto Rico/8/1934 H1N1, as set forth in GenBank Accession No. AF389117.1). The locations of amino acids residues within amino acids 210-237 are based on SEQ ID NO: 10. However, one of skill in the art would understand that corresponding locations in other PA endonuclease sequence are also contemplated herein. An influenza PA endonuclease polymerase that is at least about 80%, 85%, 90%, or 95% identical to SEQ ID NO: 10 can also be modified as set forth herein to include one or more mutations selected from the group consisting of a substitution at position I207, a substitution at position A215, a substitution at position S218, a substitution at position L219, a substitution at position L226, a substitution at position F229, and a substitution at position R230.

As used throughout, any influenza A virus can be modified to comprise a PB1 polymerase having one or more mutations selected from the group consisting of a leucine to glutamic acid, aspartic acid or asparagine substitution at position 319 (L319E/D/N); a threonine to glutamic acid, aspartic acid, glutamine or asparagine substitution at position 323 (T323E/D/Q/N); a serine to glutamic acid, aspartic acid, glutamine or asparagine substitution at position 338 (S338E/D/Q/N); and an isoleucine to glutamic acid, aspartic acid, glutamine or asparagine substitution at position 342 (I342E/D/Q/N). For example, the influenza A virus can be selected from the group consisting of an H2N2 virus, an H3N2 virus, an H1N1 virus, an H9N2 virus and an H5N1 virus. Optionally, the influenza A virus can be selected from the group consisting of A/Ann Arbor/6/60, A/California/04/2007, A/California/04/2009, A/Wisconsin/22/2011 and A/Quail/Hong Kong/G1/97. The influenza A virus can also be an avian influenza A virus. These include, but are not limited to, A/Chicken/Nanchang/3-120/01 H3N2, A/Hong Kong/485/1997(H5N1), A/Anhui/1/2013 (H7N9) and A/Shanghai/1/2013 (H7N9)

Resassortant influenza A viruses comprising one or more genomic segments from one or more influenza A viruses are also contemplated. More specifically, the virus includes genetic and/or polypeptide components derived from more than one parental viral strain or source. For example, a 7:1 reassortant includes 7 viral genomic segments (or gene segments) derived from a first parental virus and a single complementary viral genomic segment, e.g., encoding hemagglutinin (HA) or neuraminidase (NA), from a second parental virus. A 6:2 reassortant includes 6 genomic segments, most commonly the 6 internal genes from a first parental virus, and two complementary segments, e.g., hemagglutinin and neuraminidase, from a different parental virus. Optionally, reassortant viruses are produced by introducing vectors including the six internal genes of a viral strain selected for its favorable properties regarding vaccine production, in combination with the genome segments encoding the surface antigens (HA and NA) of a selected (e.g., pathogenic) strain. For example, the HA segment can be selected from an H1, H3 or B strain, as is routinely performed for vaccine production. Similarly, the HA segment can be selected from other pathogenic strains such as an H2 strain (e.g., H2N2), an H5 strain (e.g., H5N1), an H7 strain (e.g., H7N7) or an H9 strain (H9N2). In certain modified viruses, the internal gene segments are derived from the influenza A/Ann Arbor/6/60 strain, the influenza A/Puerto Rico/8/34/H1N1 (PR8) strain, or the influenza A/California/04/2007 H1N1 strain.

As set forth herein, modifications include, but are not limited to, mutations in the amino acid sequence of a PB1 polymerase. The one or more mutations in the PB1 polymerase can be non-naturally occurring and are produced by human intervention (e.g., by mutagenesis of cloned DNA sequences), such as induced point mutation, deletion, insertion and substitution mutants. Amino acid sequence mutations typically fall into one or more of three classes: substitutional, insertional or deletional mutations. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than from about 2 to about 6 residues are deleted at any one site within the protein molecule. Amino acid substitutions are typically of single residues but can occur at a number of different locations at once, for example in one, two, three, four, five, six, seven or more amino acids of the polypeptide sequence set forth as SEQ ID NO: 1, for example; insertions usually will be on the order of about from 1 to 10 amino acid residues; and deletions will range from about 1 to 10 residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions can be made in accordance with the following Table 1 and are referred to as conservative substitutions.

TABLE 1

Amino Acid Substitutions

| Amino Acid | Substitutions (others are known in the art) |
|---|---|
| Ala | Ser, Gly, Cys |
| Arg | Lys, Gln, Met, Ile |

TABLE 1-continued

Amino Acid Substitutions

| Amino Acid | Substitutions (others are known in the art) |
|---|---|
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Amino acid substitutions are not necessarily conservative as amino acid substitutions that change the side chain length, hydrophobicity or the polarity of a particular amino acid can also be made in order to alter the temperature sensitivity and/or increase the attenuation of virus.

In the PB1 polymerases described herein, a mutation at position 319 can be a leucine to glutamic acid, a leucine to aspartic acid or a leucine to asparagine substitution (L319E/D/N). In the PB1 polymerases described herein, a mutation at position 323 can be a threonine to glutamic acid, a threonine to aspartic acid, a threonine to glutamine, or a threonine to asparagine substitution (T323E/D/Q/N). In the PB1 polymerases described herein, a mutation at position 338 can be a serine to glutamic acid, a serine to aspartic acid, a serine to glutamine, or a serine to asparagine substitution (S338E/D/Q/N). In the PB1 polymerases described herein, a mutation at position 342 can be an isoleucine to glutamic acid, an isoleucine to aspartic acid, an isoleucine to glutamine, or an isoleucine to asparagine substitution (I342E/D/Q/N). For example, and not to be limiting, a modified influenza A comprises a PB1 polymerase having a L319E mutation or a PB1 polymerase having L319N mutation.

It is understood that SEQ ID NO: 1 is an example of a PB1 polymerase. However, other PB1 polymerases, for example SEQ ID NO: 2, SEQ ID NO: 3 or SEQ ID NO: 4 can be modified as set forth herein. The locations of the amino acids of PB1 polymerase set forth herein are based on SEQ ID NO: 1. However, it is understood that the corresponding positions in other PB1 polymerase sequences (for example SEQ ID NO: 2, SEQ ID NO: 3 or SEQ ID NO: 4) can be modified as set forth herein. A PB1 polymerase that is at least about 80%, 85%, 90%, or 95% identical to SEQ ID NO: 1 can also be modified as set forth herein. Therefore, provided herein are polypeptides comprising a PB1 polymerase wherein the polypeptide is at least about 80%, 85%, 90%, or 95% identical to SEQ ID NO: 1 and comprises one or more mutations selected from the group consisting of a leucine to glutamic acid, aspartic acid or asparagine substitution at position 319 (L319E/D/N); a threonine to glutamic acid, aspartic acid, glutamine or asparagine substitution at position 323 (T323E/D/Q/N); a serine to glutamic acid, aspartic acid, glutamine or asparagine substitution at position 338 (S338 E/D/Q/N); and an isoleucine to glutamic acid, aspartic acid, glutamine or asparagine substitution at position 342 (I342 E/D/Q/N).

Those of skill in the art readily understand how to determine the identity of two polypeptides or nucleic acids. For example, the identity can be calculated after aligning the two sequences so that the identity is at its highest level. Another way of calculating identity can be performed by published algorithms. Optimal alignment of sequences for comparison can be conducted using the algorithm of Smith and Waterman Adv. Appl. Math. 2: 482 (1981), by the alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information (http://www.ncbi.nlm.nih.gov/blast/b12seq/b12.html), or by inspection.

The PB1 polymerases of any modified influenza A virus described herein can optionally comprise one or more mutations selected from the group consisting of a lysine to glutamic acid substitution at position 391 (K391E), a glutamic acid to glycine substitution at position 581 (E581G) and an alanine to threonine substitution at position 661 (A661T).

Any of the influenza A viruses described herein, including those with one or more mutations in a PB1 polymerase, as described above, can further comprise a mutation in a PB2 polymerase. For example, the viruses can include one or more mutations in PB1 polymerase and a PB2 polymerase comprising an asparagine to serine substitution at position 265 (N265S). For example, and not to be limiting, the modified influenza A virus comprises a PB1 polymerase having a L319E mutation and a PB2 polymerase having a N265 S mutation. In another example, the modified influenza A virus comprises a PB1 polymerase having a L319N mutation and a PB2 polymerase having a N265S mutation.

Further, any of the influenza A viruses described herein can further comprise an influenza virus nucleoprotein (NP) comprising an aspartic acid to glycine substitution at position 34 (D34G).

Modifications, including the specific amino acid substitutions disclosed herein, are made by known methods. By way of example, modifications are made by site specific mutagenesis of nucleotides in the DNA encoding the polypeptide, thereby producing DNA encoding the modification, and thereafter expressing the DNA in recombinant cell culture. Techniques for making substitution mutations at predetermined sites in DNA having a known sequence are well known, and include, for example M13 primer mutagenesis and PCR mutagenesis.

As used throughout, the PB1 polymerase can be any influenza A PB1 polymerase, including but not limited to, a A/Ann Arbor/6/60 H2N2 PB1 polymerase (GenBank Accession No. AY210012.1) (SEQ ID NO: 1), a A/California/04/2009 H1N1 PB1 polymerase (GenBank Accession No. GQ377049.1) (SEQ ID NO: 2), an H3N2 A/Wisconsin/22/2011 PB1 polymerase (GenBank Accession No. KC883051.1) (SEQ ID NO: 3) and a A/Quail/Hong Kong/G1/97 H9N2 and H5N1 PB1 polymerase (GenBank Accession No. AF156421.1) (SEQ ID NO: 4). Optionally, the nucleic acid sequence set forth under GenBank Accession No. AY210012.1 (SEQ ID NO: 5), also known as a nucleic acid sequence that encodes the Master Donor Virus (MDV) PB1 can comprise one or more mutations selected from the group consisting of A99G, A1171G, G1371T, A1742G, G1981A, and C1995T. Optionally, the PB1 nucleic acid sequence from A/Ann Arbor/6/60 comprises A99G, A1171G, G1371T, A1742G, G1981A, and C1995T.

As used throughout, the PB2 polymerase can be any influenza A PB2 polymerase, including but not limited to A/Ann Arbor/6/60 H2N2 PB2 polymerase (GenBank Accession No. AY209938) (SEQ ID NO: 6), A/Quail/Hong Kong/G1/97 H2N2 PB2 polymerase (GenBank Accession No. AF156435) (SEQ ID NO: 7), A/Shanghai/02/2013 H7N9 PB2 polymerase (Gen Bank Accession No. KF021594) (SEQ ID NO:8) or A/Chicken/Nanchang/3-120/2001 H3N2 PB2 polymerase (Gen Bank Accession No. AY180761) (SEQ ID NO: 9).

Recombinant nucleic acids encoding a PB1 polymerase of an influenza A virus, wherein the nucleic acid encodes a PB1 polymerase having one or more mutations selected from the group consisting of a leucine to glutamic acid, aspartic acid or asparagine substitution at position 319 (L319E/D/N); a threonine to glutamic acid, aspartic acid, glutamine or asparagine substitution at position 323 (T323E/D/Q/N); a serine to glutamic acid, aspartic acid, glutamine or asparagine substitution at position 338 (S338E/D/Q/N); and an isoleucine to glutamic acid, aspartic acid, glutamine or asparagine substitution at position 342 (I342E/D/Q/N) are also provided. Further provided is a nucleic acid encoding a PB1 polymerase comprising one or more mutations selected from the group consisting of a leucine to glutamic acid, aspartic acid or asparagine at position 319 (L319E/D/N); a threonine to glutamic acid, aspartic acid, glutamine or asparagine at position 323 (T323E/D/Q/N); a serine to glutamic acid, aspartic acid, glutamine or asparagine at position 338 (S338E/D/Q/N); and an isoleucine to glutamic acid, aspartic acid, glutamine or asparagine at position 342 (I342 E/D/Q/N) and one or mutations selected from the group consisting of a lysine to glutamic acid substitution at position 391 (K391E), a glutamic acid to glycine substitution at position 581 (E581G) and an alanine to threonine substitution at position 661 (A661T). Further provided are nucleic acids that encode both PB1 and PB2 polymerases having one or more mutations and compositions comprising nucleic acids that encode PB1 and PB2 polymerases with one or more mutations.

As used throughout, the term recombinant means that the material (e.g., a nucleic acid or protein) has been artificially or synthetically (i.e., non-naturally) altered by human intervention. It is understood that, when referring to a virus, e.g., an influenza A virus, the virus is recombinant when it is produced by or modified by the expression of a recombinant nucleic acid.

As used herein, nucleic acid refers to single or multiple stranded molecules which can be DNA or RNA, or any combination thereof, including modifications to those nucleic acids. For example, the nucleic acid can be a cDNA. The nucleic acid may represent a coding strand or its complement, or any combination thereof. The nucleic acid can be directly cloned into an appropriate vector, or, if desired, can be modified to facilitate the subsequent cloning steps. Such modification steps are routine, an example of which is the addition of oligonucleotide linkers which contain restriction sites to the termini of the nucleic acid. General methods are set forth in Sambrook et al. (2012) Molecular Cloning—A Laboratory Manual (4th ed.) Vol. 1-3, Cold Spring Harbor Laboratory, Cold Spring Harbor Press, N.Y., (Sambrook).

The nucleic acids disclosed herein can be in any vector that can be used for the production of influenza virus in a host cell. The vector can direct the in vivo or in vitro synthesis of any of the polypeptides described herein, including, but not limited to PB1 and/or PB2 polymerases. One or more of the vectors described herein can be part of a multi-vector system used to produce an influenza A virus. The vector is contemplated to have the necessary functional elements that direct and regulate transcription of the inserted nucleic acid. These functional elements include, but are not limited to, a promoter; regions upstream or downstream of the promoter, such as enhancers that may regulate the transcriptional activity of the promoter; an origin of replication; appropriate restriction sites to facilitate cloning of inserts adjacent to the promoter; antibiotic resistance genes or other markers which can serve to select for cells containing the vector or the vector containing the insert; RNA splice junctions; a transcription termination region; or any other region that may serve to facilitate the expression of the inserted gene or hybrid gene (See generally, Sambrook et al. (2012)). The vector, for example, can be a plasmid. The vectors can contain genes conferring hygromycin resistance, ampicillin resistance, gentamicin resistance, neomycin resistance or other genes or phenotypes suitable for use as selectable markers.

As used throughout, a host cell is a cell that contains one or more of the nucleic acids disclosed herein, including any of the nucleic acids in a vector, and supports the replication and/or expression of the nucleic acids, and optionally production of one or more encoded products including a polypeptide and/or a virus. Host cells can be prokaryotic cells, such as E. coli, or eukaryotic cells, such as yeast, insect, amphibian, avian or mammalian cells, including human cells. Examples of host cells include, but are not limited to, Vero (African green monkey kidney) cells, Per.C6 cells (human embryonic retinal cells), BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), CEK cells, primary human lung cells, bronchial epithelial cells, COS cells (e.g., COS1, COS7 cells) and any other mammalian or avian cells that can be used to produce or propagate an influenza virus. The term host cell encompasses combinations or mixtures of cells including, but not limited to mixed cultures of different cell types or cell lines.

Any of the modified influenza A viruses described herein can be a live attenuated influenza A virus with reduced growth from about 37° C. to about 39° C., as compared to a wildtype influenza A virus or an influenza A virus comprising a PB1 polymerase lacking one or more mutations selected from the group consisting of a leucine to glutamic acid, aspartic acid or asparagine substitution at position 319 (L319E/DN); a threonine to glutamic acid, aspartic acid, glutamine or asparagine substitution at position 323 (T323E/D/Q/N); a serine to glutamic acid, aspartic acid, glutamine or asparagine substitution at position 338 (S338E/D/Q/N); and an isoleucine to glutamic acid, aspartic acid, glutamine or asparagine substitution at position 342 (I342E/D/Q/N). Optionally, the modified influenza A virus is a live attenuated influenza A virus with reduced growth from about 37° C. to about 39° C. as compared to PR8 LAIV or any other LAIV that does not comprise at least one mutation selected from the group consisting of: a mutation at position 319, a mutation at position 323, a mutation at position 338 and a mutation at position 342. Optionally, the modified influenza A virus is a live attenuated influenza A virus with reduced growth from about 37° C. to about 39° C. as compared to a live attenuated virus comprising SEQ ID NO: 1, 2, 3 or 4.

For example, the modified influenza A virus can have reduced growth at about 37° C., 38° C. or 39° C. or any temperature in between. Further, the modified influenza A virus can have reduced growth at about 37° C.-38° C. or at about 38° C.-39° C. Optionally, the modified influenza A virus grows at temperatures between about 32° C.-34° C. and has a reduction in growth at temperatures greater than about 34° C. In this way, the modified influenza A virus can grow, for example, in the upper respiratory tract where temperatures are about 32° C.-34° C., and stimulate an immune reaction, without producing symptoms in the lower respiratory tract where temperatures are about 37° C.-38° C. Optionally, the modified influenza A virus is attenuated at temperatures between about 32° C.-34° C. as well as between temperatures of about 37° C. to about 39° C. The degree of attenuation does not have to be the same at temperatures between about 32° C.-34° C. and at temperatures between about 37° C. to about 39° C., as the reduction in growth at 32° C.-34° C. can be about the same or less than the reduction in growth at about 37° C. to about 39° C. Optionally, the virus exhibits at least about a 100-fold or greater reduction in titer at about 39° C. relative to titer at about 34° C. Optionally, the modified virus exhibits an increase in the ratio of viral particles to infectious virions (particles/plaque forming units (pfu) ratio) at about 37° C. to about 39° C. As used throughout, the particle to pfu ratio is the number of viral particles required to form one plaque in a plaque assay.

As used throughout, ranges can be expressed herein as from about one particular value, and/or to about another particular value. When such a range is expressed, another aspect includes from the one particular value and/or to the other particular value. Similarly, when values are expressed as approximations, by use of the antecedent "about" it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as about that particular value in addition to the value itself. For example, if the value 10 is disclosed, then "about 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as any value between 10 and 15. It is also understood that each unit between two particular units are also disclosed. For example, if 10 and 15 are disclosed, then 11, 12, 13, and 14 are also disclosed.

A reduction or a decrease in growth can be a decrease of about 10, 20, 30, 40, 50, 60, 70, 80, 90, 100% or any percentage in between as compared to an influenza A virus comprising a PB1 polymerase lacking at least one mutation selected from the group consisting of: a mutation at position 319, a mutation at position 323, a mutation at position 338 and a mutation at position 342. Growth indicates viral quantity as indicated by titer, plaque size or morphology, particle density or other measures known to those of skill in the art. A reduction or decrease in growth can also be a reduction or decrease in replication of about 10, 20, 30, 40, 50, 60, 70, 80, 90, 100% or any percentage in between as compared to an influenza A virus comprising a PB1 polymerase lacking at least one mutation selected from the group consisting of: a mutation at position 319, a mutation at position 323, a mutation at position 338 and a mutation at position 342.

Further provided is an immunogenic composition comprising any of the modified influenza A viruses disclosed herein and a pharmaceutically acceptable carrier to stimulate an immune response against one or more strains of influenza virus. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject. One of skill in the art would know how to select a carrier in order to minimize allergic and other undesirable effects and to suit the particular route of administration. Optionally, the composition can further comprise an adjuvant. Adjuvants are known to those of skill in the art and include, for example, aluminum salts, oil-in water adjuvants (for example, MF59 or AS03), CpG adjuvants and lipids.

Suitable carriers and their formulations are described in *Remington: The Science and Practice of Pharmacy, 22nd edition*, Loyd V. Allen et al, editors, Pharmaceutical Press (2012). Examples of pharmaceutically acceptable carriers include, but are not limited to, sterile water, saline, buffered solutions like Ringer's solution, glycerol solutions, ethanol, dextrose solutions, allantoic fluid from uninfected chicken eggs (i.e., normal allantoic fluid) or combinations thereof. The pH of the solution is generally about 5 to about 8 or from about 7 to 7.5. The preparation of such solutions insuring sterility, pH, isotonicity, and stability is effected according to protocols established in the art.

Other carriers include sustained release preparations such as semipermeable matrices of solid hydrophobic polymers containing the immunogenic composition. Matrices are in the form of shaped articles, e.g., films, liposomes, or microparticles. Certain carriers may be more preferable depending upon, for instance, the route of administration and concentration of composition being administered. Carriers are those suitable for administration of the compositions disclosed herein, to humans or other subjects.

Also provided is a method for eliciting an immune response against an influenza virus in a subject comprising administering an effective dose or doses of any of the immunogenic compositions described herein. In the methods disclosed herein, the immune response can be an innate and/or an adaptive immune response. An immune response can be an antibody response against one or more strains of influenza and/or a T cell mediated response.

As used throughout, a subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with or at risk of developing an influenza infection. The term patient or subject includes human and veterinary subjects.

According to the methods taught herein, the subject is administered an effective amount of the agent, e.g., an immunogenic composition comprising a modified influenza A virus. The terms effective amount and effective dosage are used interchangeably. The term effective amount is defined as any amount necessary to produce a desired physiologic response (i.e., an immune response). Effective amounts and schedules for administering the agent may be determined empirically, and making such determinations is within the skill in the art. The dosage ranges for administration are those large enough to produce the desired effect (e.g., eliciting an immune response to the antigen of interest, i.e. influenza A). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and the agent can be administered in one or more dose administrations daily, for one or multiple days, including a prime and boost paradigm, as needed.

The compositions are administered via any of several routes of administration, including, but not limited to, orally, parenterally, intravenously, intramuscularly, subcutaneously, transdermally, nebulization/inhalation, or by installation via bronchoscopy. Optionally, the composition is administered by oral inhalation, nasal inhalation, or intranasal mucosal administration. Administration of the compositions by inhalant can be through the nose or mouth via delivery by spraying or droplet mechanism, for example, in the form of an aerosol. A form of administration that results in an immune response can be used by one of skill in the art to optimize the response.

In any of the methods described herein, the immunogenic compositions can be used alone or in combination with one or more therapeutic agents such as, for example, antiviral compounds for the treatment of influenza. These include, but are not limited to, amantadine, rimantadine, ribavirin, zanamavir (Relenza®) and oseltamavir (Tamiflu®).

Further provided is a method of treating or reducing the risk of an influenza infection in a subject, comprising administering to a subject with an influenza infection or at risk of exposure to an influenza infection an effective dose of any of the immunogenic compositions described herein.

For purposes of vaccines, the subject may be healthy and without higher risk than the general public. A subject at risk of developing an influenza infection, however, can be predisposed to contracting an infection (e.g., persons over 65, persons with asthma or other chronic respiratory disease, young children, pregnant women, persons with a hereditary predisposition, persons with a compromised immune system or by being in an environment that facilitates the passage of an influenza infection). A subject currently with an infection has one or more than one symptom of the infection. These symptoms include, but are not limited to, fever, sore throat, cough, muscle aches, headache, fatigue, vomiting and diarrhea. The subject currently with an influenza infection may have been diagnosed with an influenza infection.

The methods and compositions as described herein are useful for both prophylactic and therapeutic treatment. For prophylactic use, a therapeutically effective amount of the compositions described herein are administered to a subject prior to onset (e.g., before obvious signs of infection) or during early onset (e.g., upon initial signs and symptoms of infection). Prophylactic administration can occur for several days to years prior to the manifestation of symptoms of the infection. Prophylactic administration can be used, for example, in the preventative treatment of subjects diagnosed with a predisposition to influenza infection. Therapeutic treatment involves administering to a subject a therapeutically effective amount of the agents described herein after diagnosis or development of infection.

As used herein the terms treatment, treat, or treating refers to a method of reducing one or more of the effects of the infection or one or more symptoms of the infection by eliciting an immune response in the subject. Thus in the disclosed method, treatment can refer to a 10%, 20%, 30%, 40%, 50%, 60%, 70%, 80%, 90%, or 100% reduction in the severity of an established infection or a symptom of the infection. For example, a method for treating an infection is considered to be a treatment if there is a 10% reduction in one or more symptoms of the infection in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the infection or disease or symptoms of the infection or disease.

As used herein, reducing the risk of an influenza infection, refers to an action, for example, administration of a therapeutic agent (e.g., a composition disclosed herein) to a subject at risk of exposure to an influenza infection, that occurs prior to exposure or at about the same time a subject begins to show one or more symptoms of the infection, which inhibits or delays onset or exacerbation or delays recurrence of one or more symptoms of the infection. As used herein, references to decreasing, reducing, or inhibiting include a change of 10%, 20%, 30%, 40%, 50%, 60%, 70%, 80%, 90% or greater as compared to a control level. For example, the disclosed methods are considered to reduce the risk of infection if there is about a 10% reduction in onset, exacerbation or recurrence of infection, or symptoms of infection in a subject exposed to an infection when compared to control subjects exposed to an infection that did not receive a composition for decreasing infection. Thus, the reduction in onset, exacerbation or recurrence of infection can be about a 10, 20, 30, 40, 50, 60, 70, 80, 90, 100%, or any amount of reduction in between as compared to control subjects. For example, and not to be limiting, if about 10% of the subjects in a population do not become infected as compared to subjects that did not receive preventive treatment, this is considered prevention.

Further provided is a method of producing the influenza A viruses disclosed herein comprising (a) transfecting a population of host cells with one or more vectors comprising (i) nucleic acid sequences encoding the internal genome segments of an influenza A virus and (ii) a nucleic acid encoding a PB1 polymerase having one or more mutations selected from the group consisting of a leucine to glutamic acid, aspartic acid or asparagine substitution at position 319 (L319E/D/N); a threonine to glutamic acid, aspartic acid, glutamine or asparagine substitution at position 323 (T323E/D/Q/N); a serine to glutamic acid, aspartic acid, glutamine or asparagine substitution at position 338 (S338 E/D/Q/N); and an isoleucine to glutamic acid, aspartic acid, glutamine or asparagine substitution at position 342 (I342 E/D/Q/N); (b) culturing the host cells; and c) recovering the modified influenza A virus. Methods for producing influenza virus are known to those of skill in the art. It is understood that other internal genes encoding mutant sequences, for example, PB2 and NP, described herein can be used in the methods provided herein to produce modified influenza viruses comprising a mutant PB1 polymerase, a mutant PB2 polymerase and/or a mutant NP.

In the production methods described herein, one or more plasmids incorporating the internal genes of an influenza master virus strain, (i.e., PB1, PB2, PA, NP, M, NS1 and NS)

are transfected into suitable host cells in combination with hemagglutinin and neuraminidase segments. See, for example, U.S. Pat. No. 8,354,114, incorporated herein by reference. Optionally, the hemagglutinin and neuraminidase segments can be from a strain predicted to cause significant local or global influenza infection. Typically, the master strain is selected on the basis of desirable properties relevant to vaccine administration. For example, for vaccine production, e.g., for production of a live attenuated vaccine, the master donor virus strain can be selected for an attenuated phenotype, cold adaptation and/or temperature sensitivity. For example, Influenza A strain A/Ann Arbor/6/60 can be the master donor virus (see, for example, Chan et al., *Virology* 380: 304-311 (2008). Following replication of the reassortant virus in cell culture at appropriate temperatures for efficient recovery, for example, at temperatures equal to or less than about 35° C., such as from about 32° C. to 35° C., from about 32° C. to about 34° C., or from about 32° C. to about 33° C., the reassortant virus is recovered. Optionally, the recovered virus can be inactivated using a denaturing agent such as formaldehyde or β-propiolactone. Optionally, in the production methods provided herein, the viruses can be further amplified in chicken eggs.

Further provided is a method for producing an influenza vaccine comprising (a) infecting a population of cells with any of the viruses described herein; (b) culturing the cells; (c) harvesting the virus from the culture of step (b); and (d) preparing a vaccine with the harvested virus.

Once the virus is harvested from a cell culture, the virus can be formulated and administered as a composition, according to known methods, as an immunogenic composition to induce an immune response in an animal, e.g., a mammal. Optionally, the immunogenic composition can be formulated as an inactivated vaccine. Methods are well-known in the art for determining whether such inactivated vaccines have maintained similar antigenicity to that of the clinical isolate or a high growth strain derived therefrom. As set forth above, an immunogenic composition can be administered via all the routes conventionally used or recommended for an immunogenic composition. The immunogenic composition can be formulated as an injectable or sprayable liquid, or as a formulation which has been freeze-dried or dried by atomization or air-dried, etc. The immunogenic composition can also be formulated for administration via syringe or by means of a needle-free injector for intramuscular, subcutaneous or intradermal injection. The immunogenic composition can also be administered by means of a nebulizer capable of delivering a dry powder or a liquid or aerosolized spray to the mucous membranes.

A complete immunogenic composition can be concentrated by ultrafiltration and then purified by zonal centrifugation or by chromatography. Optionally, it can be inactivated before or after purification using formalin or β-propiolactone, for example.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

The current live attenuated influenza vaccine (LAIV) is recommended as the primary vaccination strategy for healthy subjects aged 2 to 49 years, because of its greater efficacy and ease-of-use than the traditional inactivated influenza vaccine in this age group. However, the current LA IV is not recommended for pregnant women, children under two years of age, persons with a compromised immune system, (for example, persons with REV/AIDS), or persons at high risk for complications from influenza.

The current LAIV vaccine was originally derived through cold adaptation, and subsequent work determined that the attenuating gene segments correspond to the viral polymerase (PB1, PB2, PA) and nucleoprotein (NP). Introduction of the attenuating PB2 segment into the genetic background of a seasonal influenza virus background resulted in temperature sensitivity and attenuation, which could be overcome by serial passage of virus at elevated temperatures.

These phenotypic revertant viruses were analyzed with the goal of understanding the molecular mechanism underlying the attenuation of LAIV. Methods for isolating and characterizing mutant viruses, including characterization of temperature-sensitivity are described in Treanor et al. ("Evaluation of the genetic stability of temperature-sensitive PB2 gene mutation of the influenza A/Ann Arbor/6/60 cold-adapted vaccine virus," *J. Virol.* 68(12): 7684-8 (1994)) and Cox et al. ("Development of a Mouse-Adapted Live Attenuated Influenza Virus That Permits In Vivo Analysis of Enhancements to the Safety of Live Attenuated Influenza Virus Vaccine, *Journal of Virology* 89(6): 3421-3426 (2015)) which are hereby incorporated in their entireties by this reference.

Mutations that result in substitutions at position 319 of PB1 (L319Q, L319E and L319N) were made using the methods described herein. The polymerase activity of the mutant was assayed using a minigenome assay described in Bussey et al. ("PA residues in the 2009 H1N1 pandemic influenza virus enhance avian influenza virus polymerase activity in mammalian cells," *J. Virol.* 85(14): 7020-8 (2011)), which is hereby incorporated in its entirety by this reference. It was found that mutations in the PB1 gene (at residue 319) were sufficient to reverse the temperature sensitive phenotype of the viral RNA polymerase, conferred by the LAW PB2 gene segment.

Growth studies were performed by constructing and characterizing mutant viruses as set forth in Treanor et al. Viruses were characterized for temperature sensitivity in the following manner: confluent 6 well plates of MDCK cells or A549 cells were infected at a multiplicity of infection (MOI) of 0.01 with the ts single gene replacement virus and incubated at 34, 37 and 39° C. for 72 hours in DMEM containing 0.3% bovine serum albumin (BSA) and tosylsulfonylphenylalanyl chloromethyl ketone (TPCK)-trypsin (1 µg/ml). Every 12 hours (at 12, 24, 48, 72 and 96 hours post-infection) a sample of the culture supernatant was harvested and replaced with fresh media. These samples were clarified by centrifugation and stored at −80° C. The samples were then analyzed for viral titer through TCID-50 analysis, using hemagglutination of turkey red blood cells (RBCs) as the endpoint, as described in Bussey et al.

The virus used in this analysis possessed the PB2 segment of cold adapted temperature sensitive and attenuated A/Ann Arbor/6/60 (Genbank ID: AY209938.1) in the background of A/Korea/1982 (see Treanor et al.). As set forth above, the PB2 segment of a seasonal human influenza A virus strain (A/Korea/82 H3N2) was replaced with the PB2 segment from the cold passaged isolate of A/AnnArbor/6/60. The resulting single gene replacement virus is temperature sensitive (ts) for growth at elevated temperatures. This virus stock was subjected to serial passage at increasing temperatures, in order to identify phenotypically revertant single gene replacement viruses. The ts PB2 single gene replacement virus was subjected to plaque purification and individual plaques were analyzed for their temperature dependent growth properties. The plaque purified viruses were expected to have growth at 34° C. and 37° C., but not at 39° C. (see FIG. 1). A virus that had reduced growth at 37° C. as well as at 39° C. was purified.

Figure 2:
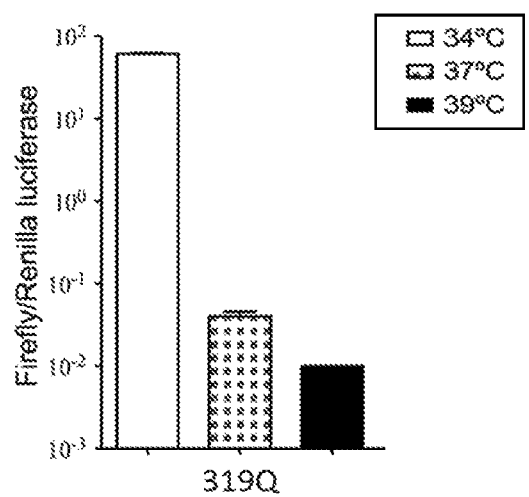
FIG. 2 shows that the PB1 319Q mutation significantly reduces functional activity of the human influenza A virus RNA polymerase at 37° C. The polymerase activity of the indicated polymerases was characterized in human HEK-293FT cells by quantifying luciferase activity in the clarified cell lysates of cells transfected with PB1-, PB2-, PA-, and NP-protein expression plasmids along with a reporter plasmid expressing an influenza virus-like RNA construct for firefly luciferase. The cells were incubated at the indicated temperatures. All assays utilized the same NP plasmid. Depicted is the ratio of firefly to renilla luminescence. Data are averaged over a minimum of three independent experiments. Error bars represent one standard error of the mean. All plasmids used in this mini-genome assay were identical, except for the PB1 plasmid, which encoded a Q at residue 319 (as indicated). These plasmids were created from viral stocks through cloning the consensus sequence from viral growth curves into the mammalian pCAGGS expression vector.

All components of the viral polymerase were cloned into a mammalian expression vector from the viral RNA and then analyzed. Surprisingly, this system revealed a significant decrease in polymerase activity at 37° C. A number of residues were found to be unique as compared to conserved influenza sequences and their importance was examined through mutation to the conserved residue by site directed mutagenesis. A residue of interest resided in PB1, at amino acid 319, and was the substitution of a nonpolar leucine with a polar glutamine (L319Q). The PB1 L319Q mutation dramatically reduces functional activity of human influenza A virus RNA polymerase at 37° C. (see FIG. 2).

Figure 3:
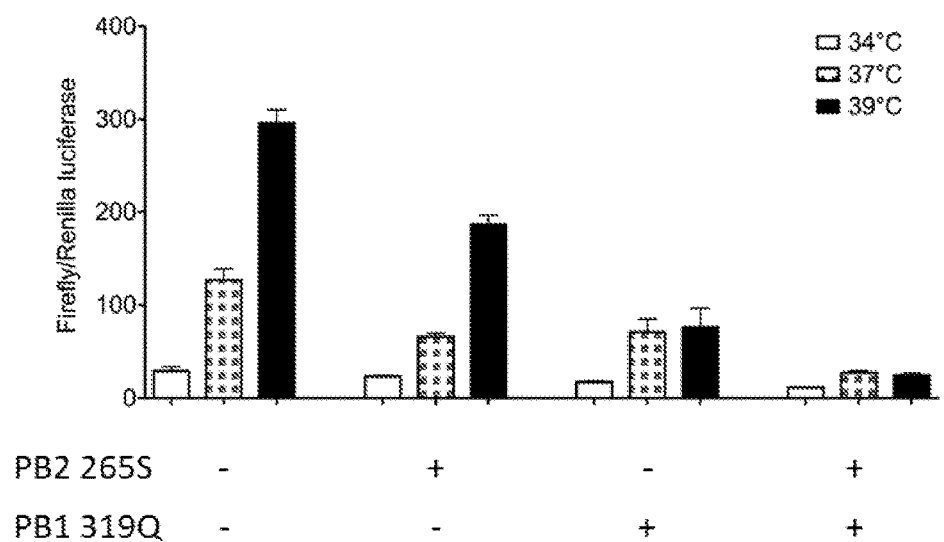
FIG. 3 shows that the PB1 L319Q mutation reduces functional activity of an avian influenza A virus RNA polymerase at 37° C. The polymerase activity of each viral polymerase was characterized in human HEK-293FT cells by quantifying luciferase activity in the clarified cell lysates of cells transfected with PB1-, PB2-, PA-, and NP-protein expression plastids along with a reporter plasmid expressing an influenza virus-like RNA construct for firefly luciferase. The cells were incubated at the indicated temperatures. Depicted is the ratio of firefly to renilla luminescence. Data are averaged over a minimum of 3 independent experiments. Error bars represent one standard error of the mean. In this experiment, all polymerase gene segments were derived from avian influenza viruses. The PA and PB2 segments were derived from A/California/04/09 H1N1, and the PB1 and NP segments were derived from A/Chicken/Nanchang/3 H3N2. Plasmids differed only at the indicated residues: (1) PB2 encoding either 265S or 265N [wild-type]; (2) encoding either 319Q or 319L [wild-type].
Figure 4:
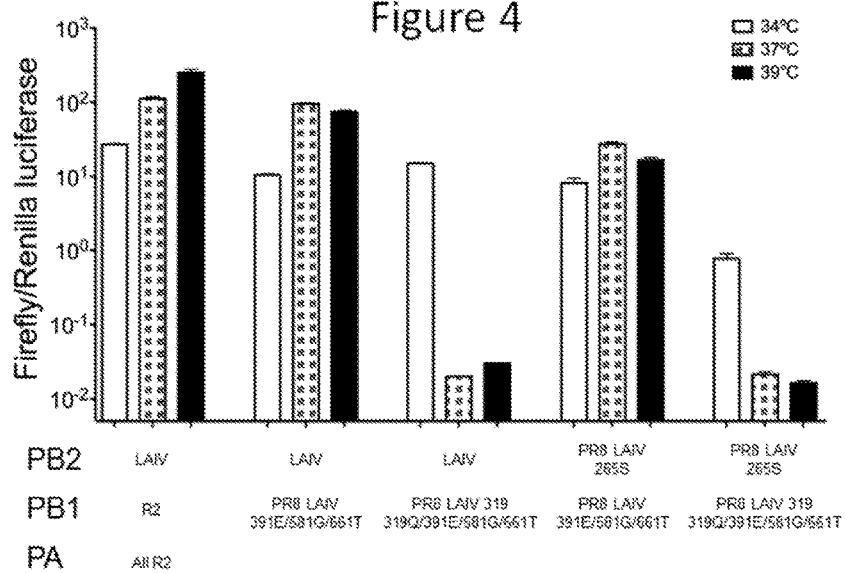
FIG. 4 shows the effects of a 319Q mutation in PB1, in combination with three mutations present in live attenuated influenza vaccine (LAIV) PB1.

The impact of this mutation on other influenza A viruses (IAV) was then examined. In these experiments an avian IAV polymerase complex, the polymerase complex from the low-pathogenicity virus, A/Chicken/Nanchang/3-120/01 H3N2, was used. Introduction of the L319Q mutation in PB1 into this polymerase also significantly reduced the functional activity of this avian influenza A virus RNA polymerase at 37° C. (FIG. 3). It was also found that a PB1 with a L319Q mutation synergizes with three mutations (K391E, E581G and A661T) found in the LAIV (FIG. 4). The polymerase activity was assayed using the minigenome assay described in Bussey et al.

Figure 5:
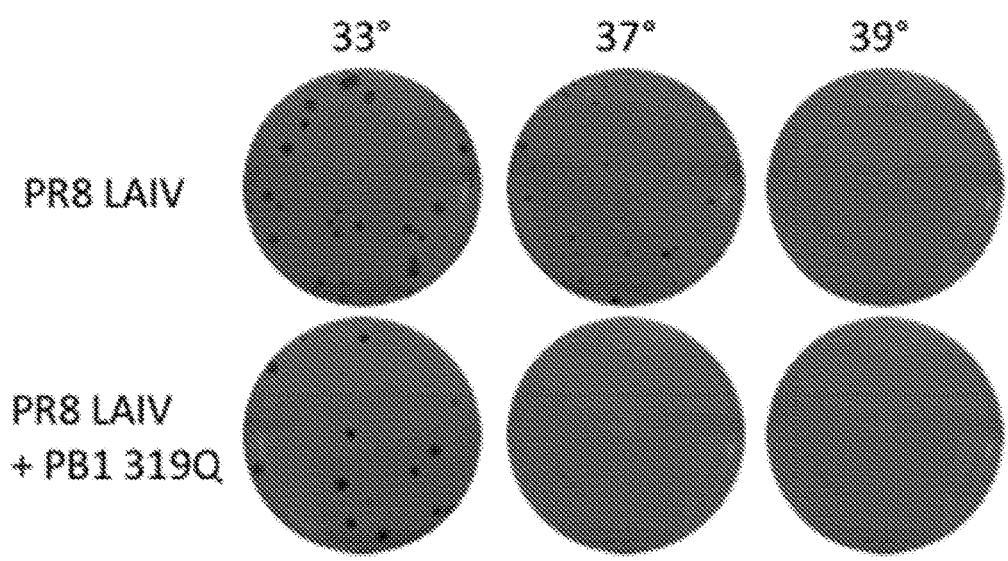
FIG. 5 shows the effects of a 319Q mutation in PB1, in combination with four mutations present in LAIV PB1.

Additional experiments were conducted to further characterize the temperature sensitivity of a modified vaccine strain virus. Viruses were created through site directed mutagenesis of the PR8 bidirectional plasmids described in Martinez-Sobrido et al. ("Generation of Recombinant Influenza Virus from Plasmid DNA," J. Vis. Exp. 42: 2057 (2010)). PR8 live attenuated influenza virus (PR8 LAIV) is a PR8 virus (cold adapted A/ANN ARBOR/6/60 virus) that has been modified to include the four amino acid mutations present in LAIV. These mutations are N265S in PB2, K391E in PB1, E581G in PB1 and A661T in PB1 as this virus already possess a glycine residue at residue 34 of NP. PR8 LAIV+PB1 319Q possesses the mutation PB1 L319Q in addition to the 4 mutations present in PR8 LAIV. All plasmids were sequenced to confirm successful site directed mutagenesis and all rescued viruses were sequenced to confirm retention of only the desired mutations. Both viruses were assayed for temperature-sensitive growth via plaque assay, as described in Bussey et al. When the four mutations of LAIV (N265S in PB2, K391E in PB1, E581G in PB1 and A661T in PB1) were added to PR8 no virus was detected by plaque assay at 39° C. However, when PB1 319Q was added in addition to the four mutations of LAIV, no virus growth occurred at 37° C. as well (FIG. 5).

Figure 6:
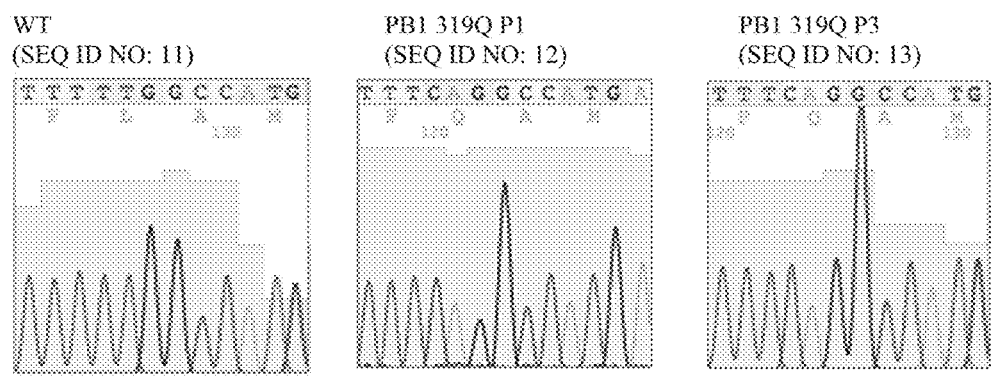
FIG. 6 shows the stability of the mutation at position 319 of PB1.

Experiments were also conducted to characterize the stability of the L319Q mutation. The stability of a glutamine at residue 319Q of PB1 was analyzed by inserting this mutation singly in the background of a wild type virus to determine whether this mutation is stable. These viruses were constructed via site-directed mutagenesis of the PR8 bidirectional plasmids described in Martinez-Sobrido et al. PB1 319Q possesses glutamine instead of the wildtype leucine at residue 319 of PB1. All plasmids were sequenced to confirm successful site-directed mutagenesis and all rescued viruses were sequenced to confirm retention of only the desired mutations. The viruses were then passaged an additional three times at 30° C., 33° C., 37° C. and 39° C. The PB1 gene was then sequenced in its entirety as described in Zhou et al. ("Single-reaction genomic amplification accelerates sequencing and vaccine production for classical and Swine origin human influenza a viruses," J. Virol. 19: 10309-13 (2009)), which is incorporated herein in its entirety by this reference. After one passage, the virus showed uniform stability. After two subsequent passages at each of 30° C., 33° C., 37° C. and 39° C., all viruses retained glutamine at this position. This shows that this mutation is stable at various temperatures in influenza A viruses (FIG. 6).

Figure 7A:
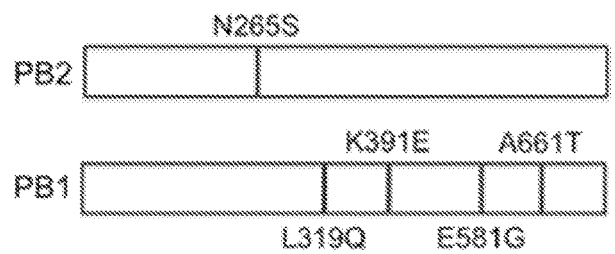
FIG. 7A shows the mutations present in influenza virus strain A/PR/8/34 (PR8) polymerase.
Figure 7B:
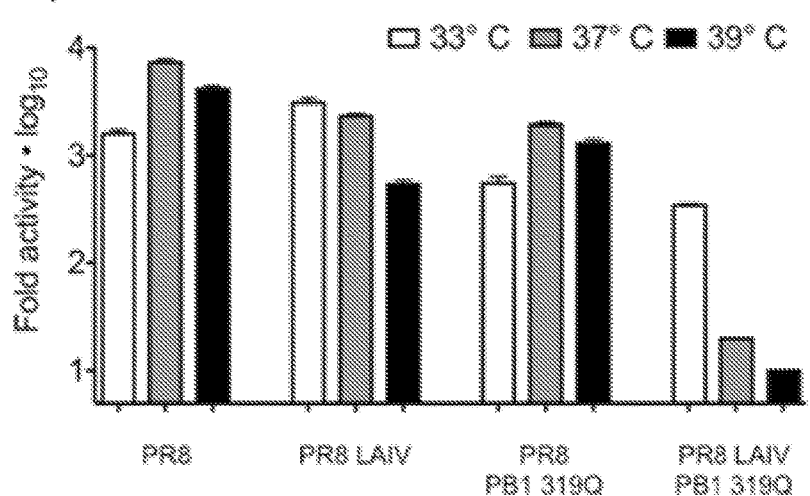
FIG. 7B shows minigenome activity of PR8, PR8 LAIV and PR8 LAIV 319Q. Minigenome assays were performed in HEK-293T cells (ATCC). Mean±standard deviation (SD) fold increase activity over a no PB2 control for triplicate transfections are plotted.

Additional growth studies were performed using the methods described herein. The natural (and universally conserved) leucine was replaced with glutamine at residue 319 of PB1 (FIG. 7A). This amino acid lies underneath the PA linker region and 30 Å from PB1 391 (the nearest amino acid mutation of LAIV). Mutating PB1 319 from leucine to glutamine in the context of the mutations of LAIV results in a dramatically altered polymerase activity profile as measured by minigenome assay (FIG. 7B) as PR8 LAIV containing 319Q shows a sharp reduction in polymerase activity at temperatures as low as 37° C. Interestingly, the introduction of PB1 L319Q alone has little to no impact on temperature sensitive polymerase activity.

Figure 7C:
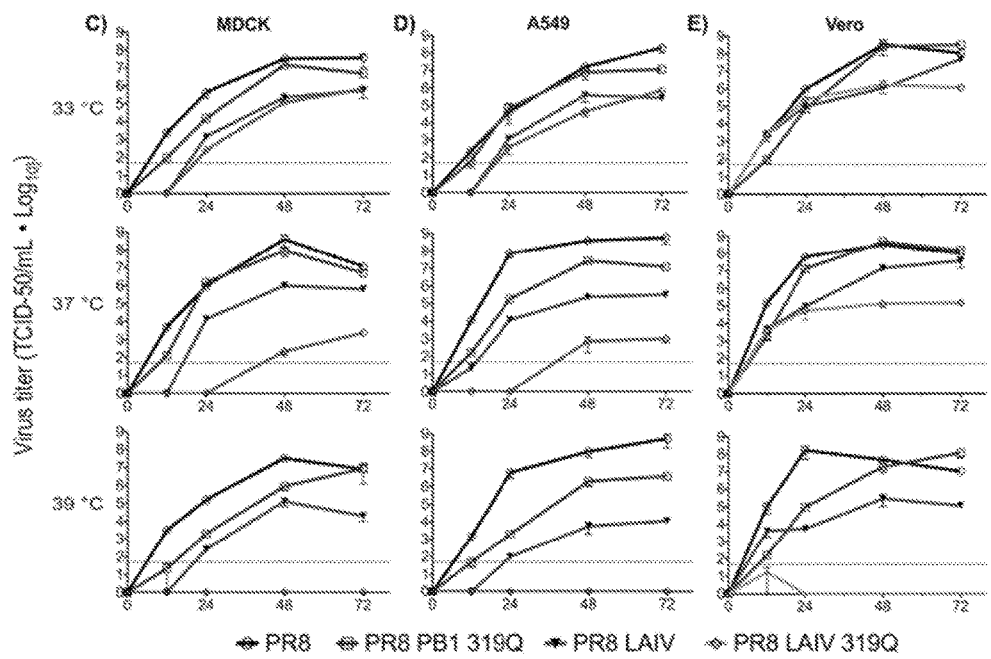
FIG. 7C shows that PR8 LAIV 319Q is more temperature sensitive than PR8 LAIV. Multicycle growth curve experiments were performed at 33° C., 37° C. and 39° C. with MDCK, A549 and Vero cells (all purchased from ATCC). Mean±SD values for triplicate infections are plotted; the dotted line denotes the limit of detection (50 TCID-50/mL.

The viruses containing either PB1 L319Q (PR8 319Q) alone or the attenuating mutations of LAIV and PB1 319Q (PR8 LAIV 319Q) were rescued and their growth was analyzed in MDCK, A549, and Vero cells. A549 cells were selected, because they are derived from the human airway, while Vero were chosen because they have a defective interferon response system. Compared to wild type viruses, PR8 containing only PB1 L319Q shows a slight reduction in replication at elevated temperatures in A549, but not MDCK or Vero cells (FIG. 7C). PR8 319Q is a cold adapted A/ANN ARBOR/6/60 virus that has been modified to include a L319Q mutation. PR8 LAIV shows impaired growth at 39° C. in all cell types tested. In contrast PR8 LAIV 319Q shows dramatically reduced replication at 37° C. and no virus was detected at 39° C. in A549 and MDCK cells. As set forth above, PR8 LAIV+PB1 319Q possesses the mutation PB1 L319Q in addition to the 4 mutations present in PR8 LAIV (N265S in PB2, K391E in PB1, E581G in PB1 and A661T in PB1). Therefore, the addition of PB1 319Q dramatically increases the temperature sensitivity of viruses containing the attenuating mutations of LAIV. Stability was also examined and the viruses retained the attenuating mutations after 10 passages in tissue culture.

In addition to determining the growth characteristics of an influenza A virus comprising a PB1 polymerase with a L319Q mutation, safety studies for this mutant virus were conducted.

Figure 8:
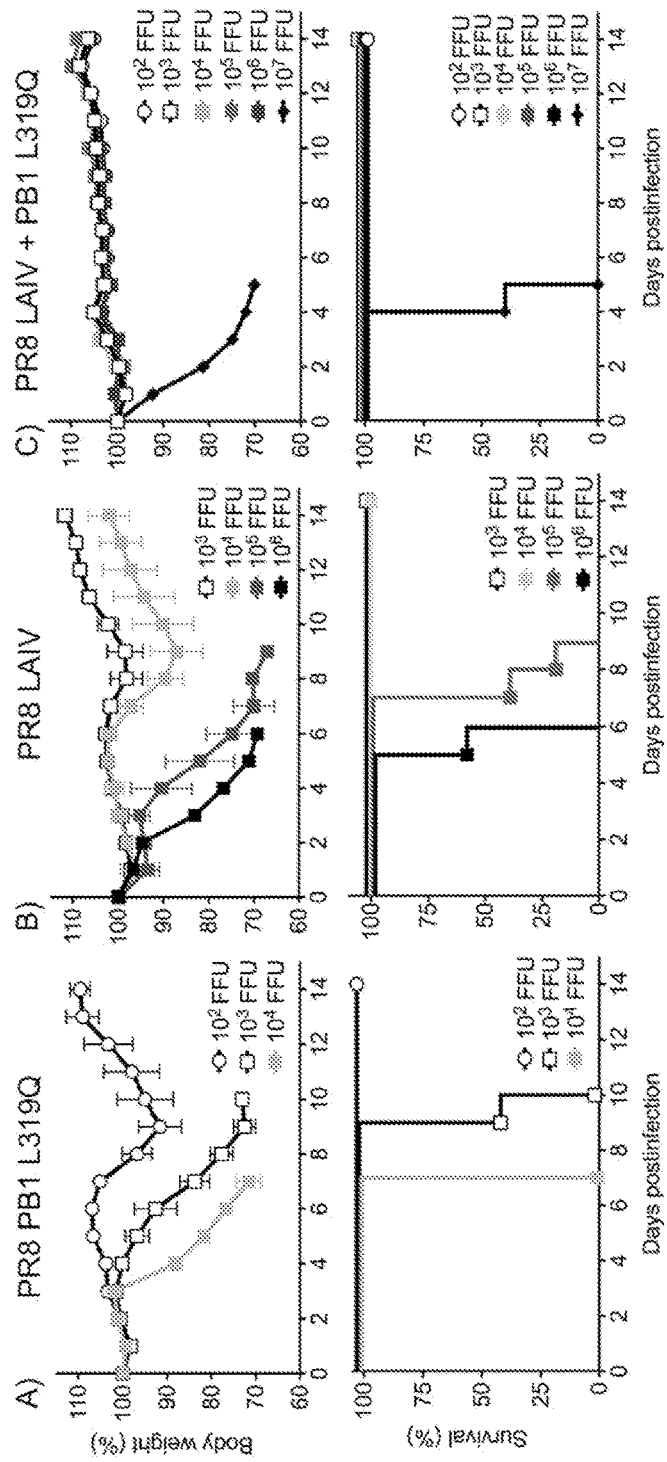
FIGS. 8A-C shows the effect of a 319Q mutation in PB1 on pathogenicity in mice alone and in combination with the mutations of LAIV (N265S in PB2, K391E, E581G and A661T in PB1). PR8 319Q, PR8 LAIV, and PR8 LAIV 319Q are attenuated in mice. Female 5- to 7-week-old B6 mice were inoculated intranasally with the indicated doses of (A) PR8 PB1 L319Q, (B) PR8 LAIV, or (C) PR8 LAIV L319Q. For 2 weeks postinfection, weight loss (above) (plotted data represent means±standard errors of the means [SEM]) and survival (below) were monitored daily (n=5-10).

For these safety studies, 5-7 week old female C57 BL/6 were purchased from Jackson Laboratory (Bar Harbor, Me.). Mice were inoculated intranasally after light anesthetization with increasing doses of PR8 319Q and PR8 LAIV 319Q. Data from Cox et al. (*J. Virol.* 89: 3421-3426 (2015)) on the safety of LAIV in C57/B6 mice is replicated for comparison. Addition of PB1 319Q to LAIV increased safety by 10,000 fold (from $10^2$ FFU to $10^6$ FFU), as determined by comparing maximum safe doses in mice (i.e., the maximum dose at which no weight loss was observed) as PR8 LAIV has a maximum safe dose of 100 FFU. (FIG. 8 and Table 2).

TABLE 2

| Virus | Maximum Safe Dose | PD-50 (PR8) | PD-50 (X31) |
|---|---|---|---|
| PR8 | 1 FFU[12] | ND | ND |
| PR8 PB1 319Q | 1 FFU | ND | ND |
| PR8 LAIV | 100 FFU[12] | 20 FFU | 30 FFU |
| PR8 LAIV PB1 319Q | 1,000,000 FFU | 400 FFU | 600 FFU |

An additional cohort of mice was treated with $10^6$ FFU of PR8 LAIV 319Q that had been exposed to UV light for 20 min. This cohort suffered no weight loss or clinical distress similar to the infected mice. Fourteen days post infection mice were bled via cheek bleeds for the collection of sera.

Figure 9A:
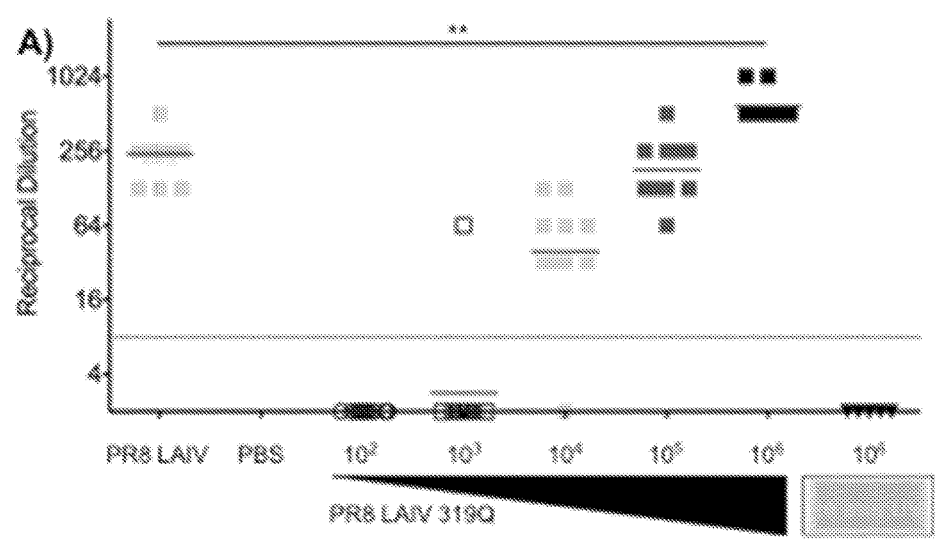
FIG. 9A shows the immunogenicity of live attenuated influenza virus (LAIV) comprising a 319Q mutation in PB1. This figure shows that replication is necessary for immunogenicity as UV inactivation renders the virus non-immunogenic.

Convalescent sera was treated with receptor destroying enzyme (BEI) for 18 hr at 37° C. The resulting sera was analyzed for its ability to block the hemagglutination of turkey red blood cells by a known quantity of virus. Sera was serially diluted in a 96 well plate, mixed with a known quantity of PR8 virus and incubated at room temperature for 30 min. 0.5% turkey red blood cells were then added to the wells and allowed to hemagluttinate. A dilution was positive if the sera was able to prevent the virus blocking the hemagluttination of the red blood cells. Depicted is the reciprocal of the lowest dilution of sera that was able to inhibit viral mediated hemagluttination. See FIG. 9 showing that PR8 LAIV 319Q retains replication-dependent immunogenicity. FIG. 9 shows that replicating virus is necessary for protection, as UV inactivated virus did not cause seroconversion. In addition, mice seroconverted at doses 1000-fold lower than the highest administered dose. Statistical analysis was performed by GraphPad Prism using one way Anova followed by Tukey's post test (**p<0.01).

Figure 9B:
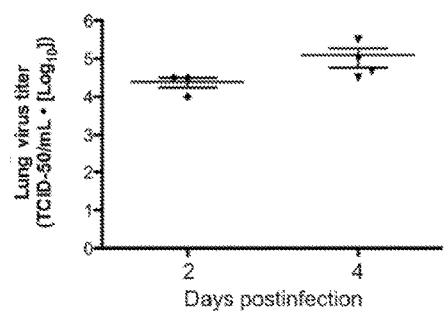
FIG. 9B shows that PR8 LAIV+PB1 L319Q replicate in vivo. Mice were inoculated with 10⁷ FFU of PR8 LAIV 319Q (n=3-4). At 2 and 4 days postinfection, lung virus titers (TCID50/mL) were determined from total lung homogenates on MDCK cells using the method of Reed and Meunch (*Journal of Epidemiology* 27: 493-497 (1938)). Lines represent mean virus lung titers±standard deviations (SD) from individual mice.

Virus replication was detected in the mouse lung with doses of $10^7$ FFU resulting in viral titers of $3 \times 10^4$ and $10^5$ on days two and four post infection respectively (FIG. 9B). These viruses were sequenced and no reversion mutants were detected. No virus was recovered from the lungs of mice infected with doses of $10^6$ or lower at 2, 3 or 4 days post infection.

Figure 10:
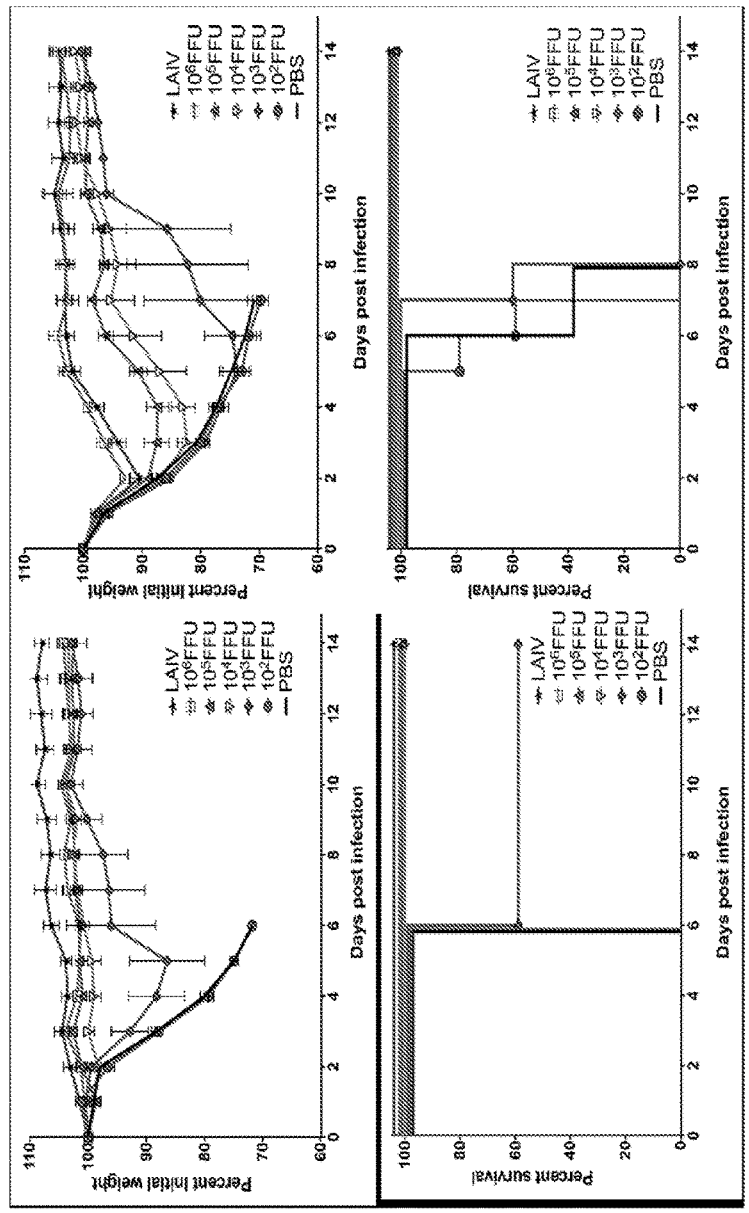
FIG. 10 shows the protective efficacy of a live attenuated influenza virus (LAIV) comprising a 319Q mutation in PB1 against homologous and heterologous lethal challenge. LAIV 319Q is protective against both homologous (matched) and heterologous (mismatched) strains of influenza. All mice that seroconverted were protected from challenge with homologous virus and all mice that seroconverted for the matched strain were also protected against the mismatched strain. Additionally, cohorts of mice that did not seroconvert were also protected suggesting T-cell mediated vaccine responses.

Twenty-one days post vaccination, mice were challenged with 100 $LD_{50}$ of PR8 (homologous) or X-31 (heterologous) virus in a total volume of 30 μL after avertin anesthetization. Weight loss and clinical signs of distress were measured daily and mice were euthanized upon losing 30% of their initial body weight or clinical signs of distress. Mean lethal dose was calculated by the method of Reed and Meunch (*Journal of Epidemiology* 27: 493-497 (1938)). FIG. 10 shows the protective efficacy of influenza viruses containing a L319Q mutation in PB1 against homologous and heterologous lethal challenge. LAIV 319Q is protective against both homologous (matched) and heterologous (mismatched) strains of influenza. LAIV 319Q provided greater protection than LAIV at matched doses of priming virus (the highest dose of each virus that did not cause weight loss), showing that this safer vaccine candidate does not have compromised efficacy. Additionally, LAIV 319Q protected mice against lethal challenge at vaccination doses of $10^3$ or greater against both homologous and heterologous challenges. This implicates T cell-mediated immunity, as none of these mice displayed seroconversion to X31 at day 15 postvaccination. All mice that seroconverted were protected from challenge with homologous virus, and all mice that seroconverted for the matched strain were also protected against the mismatched strain. Four mice that did not seroconvert in the $10^3$ FFU group were also protected against lethal challenge. These studies show that LAIV 319Q is a vaccine that exhibits 10,000-fold increased safety, while retaining robust immunogenicity in a murine model of influenza infection.

Figure 11:
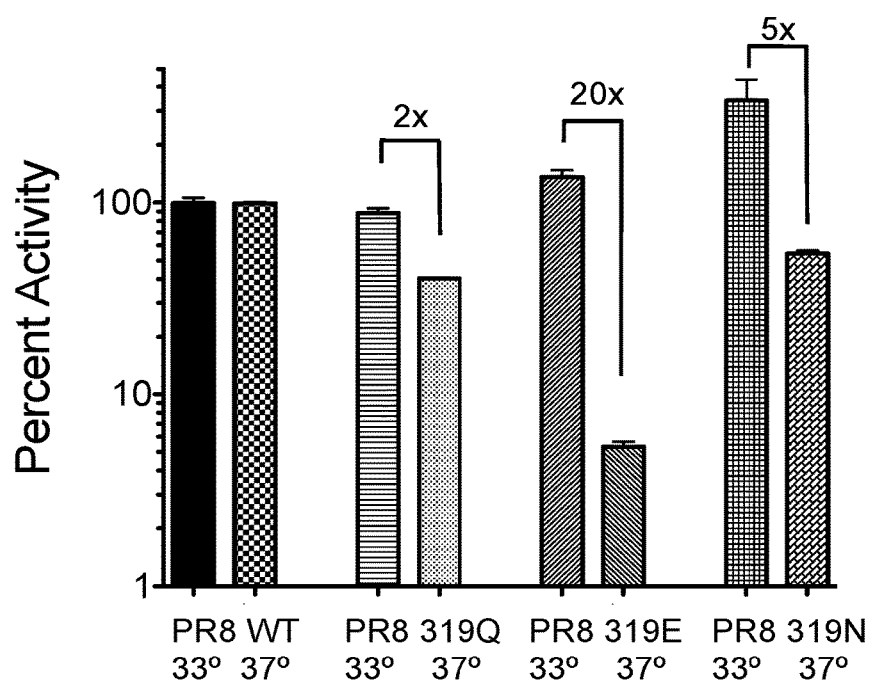
FIG. 11 shows that a L319E mutation at PB1 results in a PB1 polymerase with a 20-fold decrease in activity at 37° C. as compared to activity at 33° C.

Using the methods set forth herein, the activities of a PB1 polymerase comprising an L319E and a PB1 polymerase comprising an L319N were assayed. It was found that a L319E mutation reversed the temperature sensitive phenotype of the viral RNA polymerase, conferred by the LAIV PB2 gene segment. Surprisingly, the PB1 polymerase comprising a L319E mutation had a 20-fold decrease in activity at 37° C., as compared to a 2-fold decrease in activity for a PB1 polymerase comprising a L319Q mutation. The L319N mutation also reversed the temperature sensitive phenotype of the viral RNA polymerase, conferred by the LAIV PB2 gene segment. The PB1 polymerase comprising a L319N mutation had a 5-fold decrease in activity at 37° C., as compared to a 2-fold decrease in activity for a PB1 polymerase comprising a L319Q mutation (FIG. 11).

Figure 12:
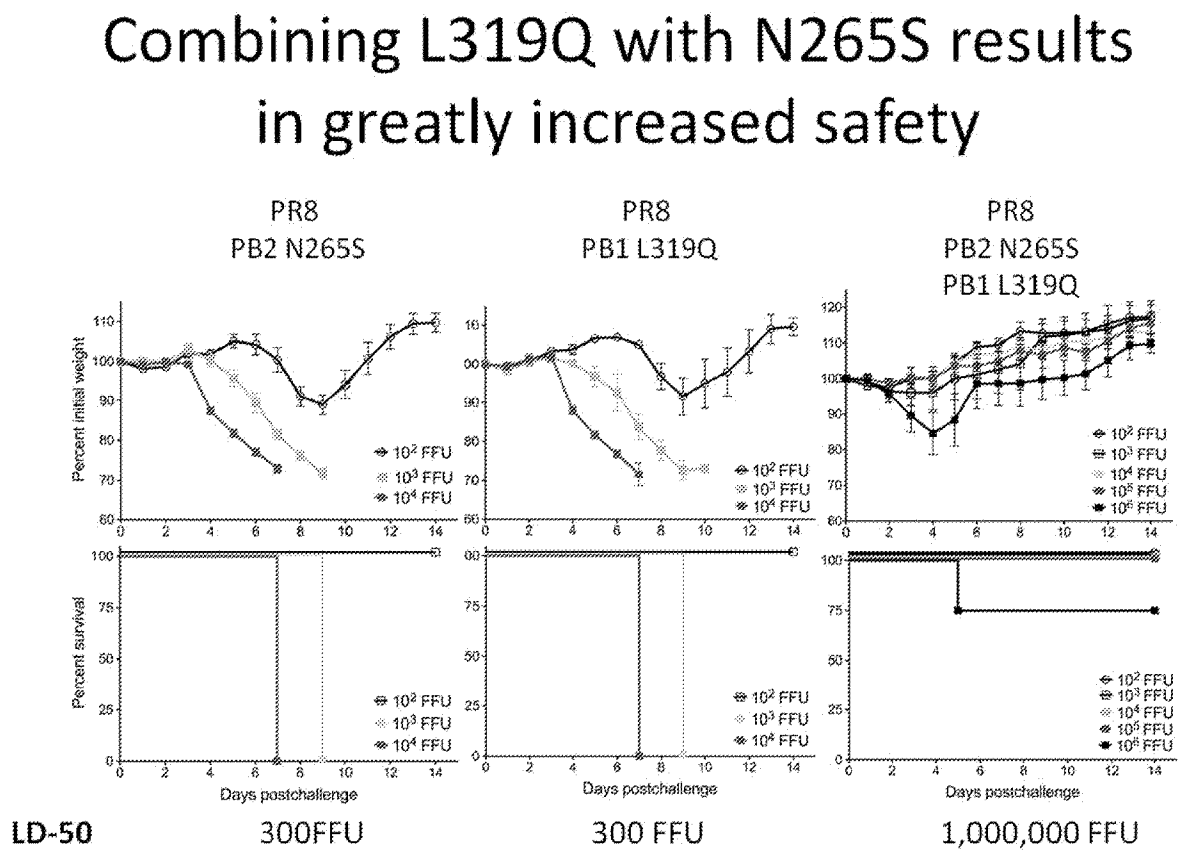
Figure 13:
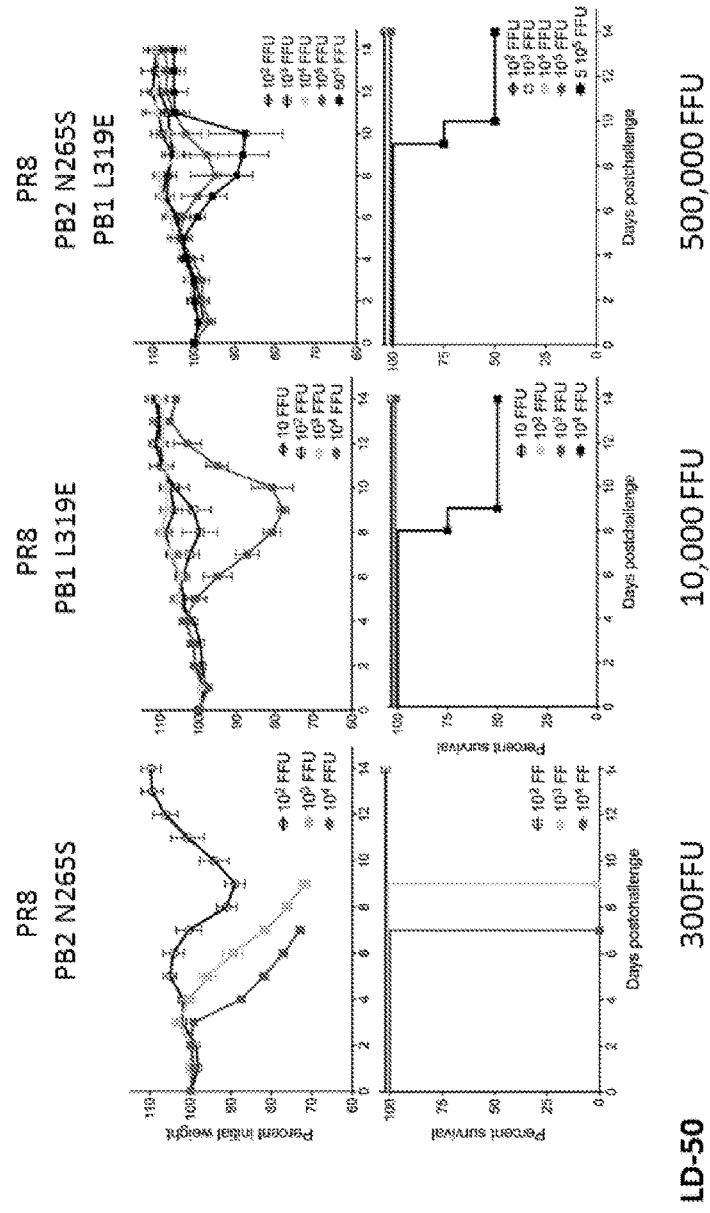
FIG. 13 shows that an influenza virus with a L319E mutation in PB1 synergizes with a N265S mutation in PB2 and results in a 300-fold increase in safety as compared to a PB1 polymerase comprising a L319Q mutation.

It was also found that a PB1 with a L319Q or a L319E mutation synergizes with a N265S mutation found in PB2 (FIGS. 12 and 13, respectively). Surprisingly, an influenza virus with a PB1 L319E mutation results in a 3000-fold increase in safety as compared to the PR8 virus and a 300 fold increase in safety as compared to an influenza virus with a PB1 L319Q mutation. This shows that, unexpectedly, changes to residue 319, for example, a Q to E substitution, can have dramatic impacts on the attenuation of the resulting viruses. Therefore, altering the amino acid identity at position 319, position 323, position 338 and/or 342 could result in viruses with varied temperature sensitivity and safety over a large range of administered doses. This could result in viruses that have greater protection at lower doses due to their enhanced safety coupled with robust growth at 33° C.

Figure 14:
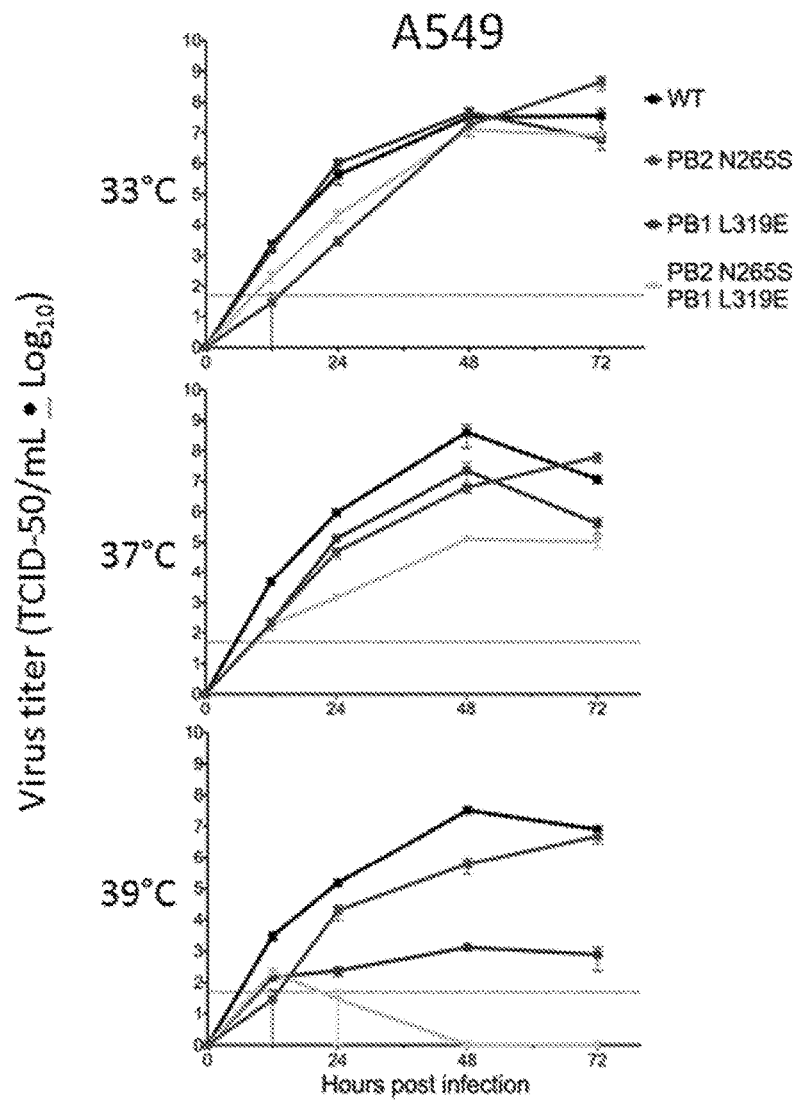
FIG. 14 shows that an influenza virus with a L319E mutation in PB1 synergizes with a N265S mutation in PB2 in A549 cells.
Figure 15:
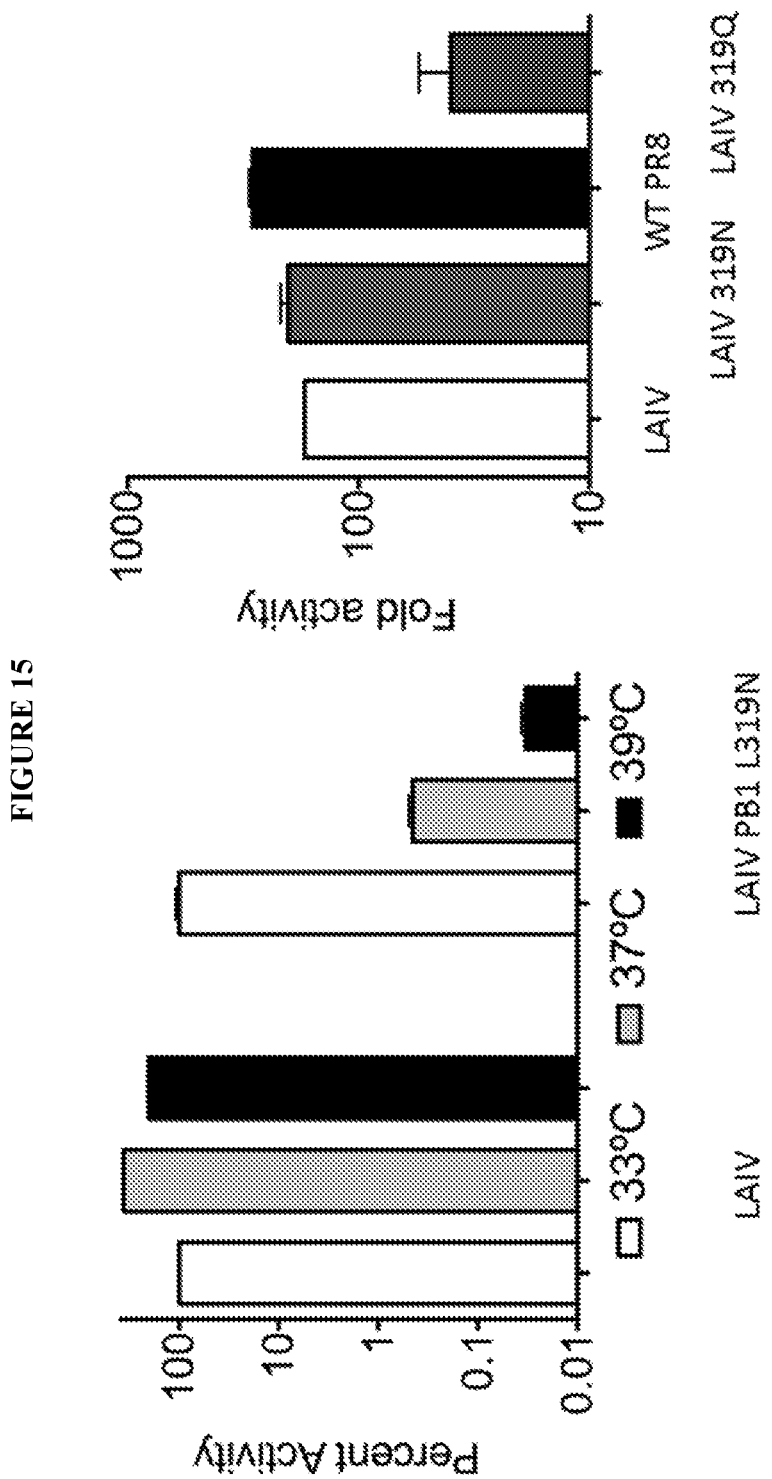
FIG. 15 shows that a live attenuated influenza virus with a PB1 polymerase comprising a L319N mutation has increased activity at 33° C. as compared to a live attenuated influenza virus with a PB1 polymerase comprising a L319Q mutation.

FIG. 14 shows that a L319E synergizes with a PB2 N265S mutation in A549 cells. Minigenome assays also showed that LAIV with a PB1 L319N mutation has increased activity at 33° C. as compared to an LAIV with a PB1 L319Q mutation (FIG. 15). Thus, L319E and L319N can be used to make live attenuated influenza viruses. These mutations can also be used to further attenuate existing live attenuated influenza viruses (LAIV), thereby increasing their safety, and allowing for its use in populations in which the vaccine is presently contraindicated.

Figure 16B:
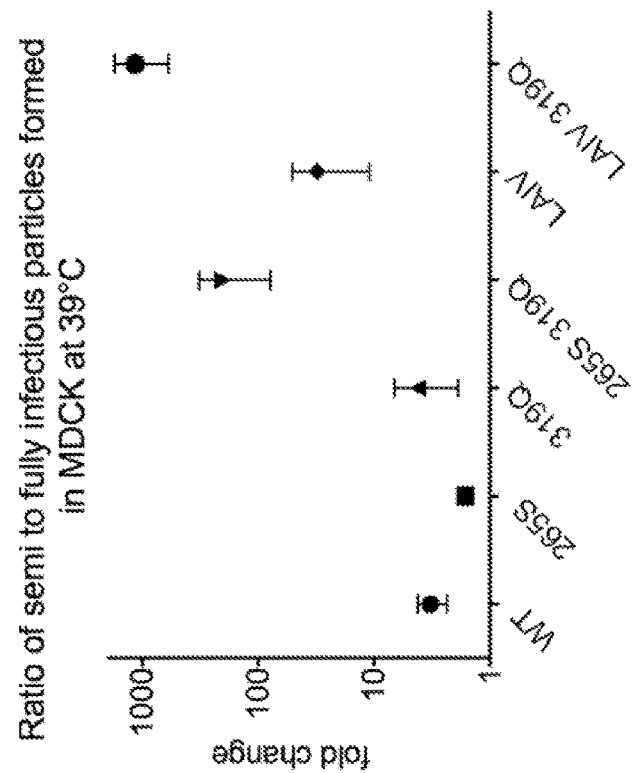
FIGS. 16A and B show that PR8 viruses containing i) 319Q and 265S, ii) LAIV or iii) LAIV and 319Q produce more protein than fully infectious viruses.
Figure 16A:
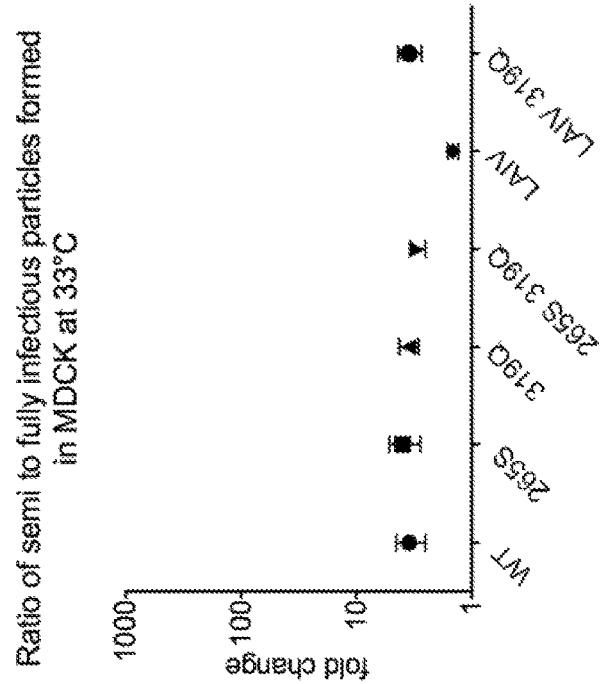

Using a protocol modified from Brooke et al. (*J. Virol.* 87(6): 3155-3162 (2013)) it was also found that PR8 viruses containing i) a L319Q mutation and a PB2 N265S mutation 2) LAIV or 3) LAIV and a L319Q mutation produce more protein than viruses (FIG. 16B). MDCK cells were infected with viruses at an MOI of 0.05 at either 33 or 39° C. After 24 hours, viruses were harvested and used to infect A549 cells for single cell flow analysis. This second infection was carried out at the permissive temperature of 33° C. and the spread of infectious virus was stopped by adding a neutralizing antibody 2 hours after infection. Sixteen hours after infection, cells were gently fixed and permeabilized and stained for HA and NA and analyzed by flow cytometry. The ratio of cells expressing only HA or NA was compared to that of cells expressing both HA and NA.

Figure 17:
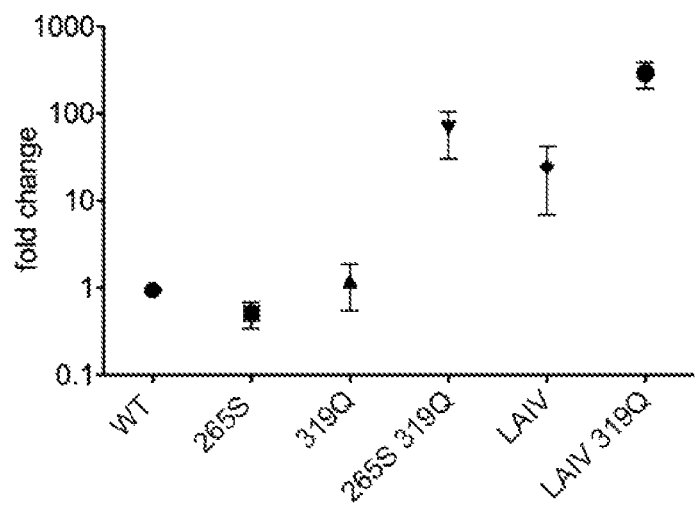
FIG. 17 shows that the ratio of infectious particle formation at 39° C. vs 33° C. for a virus comprising a N265S mutation and a L319Q mutation, LAIV and LAIV 319Q. A virus comprising a N265S mutation and a L319Q mutation, LAIV and LAIV 319Q all have a temperature sensitive increase in protein production as compared to fully infectious viruses, i.e., an increase in particle/pfu ratio.

As shown in FIG. 16B, when the first infection was carried out at 33° C., the ratio of singly expressing ($HA^+NA^-$ or $NA^+HA^-$) to fully expressing cells ($HA^+NA^+$) was comparable, and between about 3 and 6. This indicates that many of the particles produced were fully infectious. As shown in FIG. 16B, when the first infection was carried out at 39° C., a skew is seen in 265S/319Q, LAIV and LAIV 319Q, where between 30 and 1000 more singly infectious particles are produced. This indicated that, although reduced titer of these viruses is observed at elevated temperatures, these viruses are still capable of producing protein that can serve as an immunogen. FIG. 17 shows the ratio of infectious particle formation at 39° C. vs. 33° C. 265S/319Q, LAIV and LAIV 319Q have a temperature sensitive increase in protein production compared to fully infectious viruses. Therefore, including a PB1 L319Q mutation in LAIV improves LAIV by increasing the amount of protein produced while minimizing the production of virions (decreasing viral titer) that can productively infect additional cells. This decrease in titer as compared to protein production results in an increased viral particle to infectious virion ratio (particle/pfu ratio). Therefore, even if viral protein levels are not significantly altered at about 33° C. vs 39° C., the reduction in viral titer at about 39° C. as compared to viral titer at about 33° C. results in an increased particle/pfu ratio.

SEQUENCES

```
SEQ ID NO: 1
MDVNPTLLFLKVPAQNAISTTFPYTGDPPYSHGTGTGYTMDTVNRTHQYS
EKGKWTTNTETGAHQLNPIDGPLPEDNEPSGYAQTDCVLEAMAFLEESHP
GIFENSCLETMEVIQQTRVDKLTQGRQTYDWTLNRNQPAATALANTIEVF
RSNGLTANESGRLIDFLKDVIESMDKEEMEITTHFQRKRRVRDNMTKKMV
TQRTIGKKKQRLNKRSYLIRALTLNTMTKDAERGKLKRRAIATPGMQIRG
FVYFVETLARSICEKLEQSGLPVGGNEKKAKLANVVRKMMTNSQDTELSF
TITGDNTKWNENQNPRMFLAMITYITRNQPEWFRNVLSIAPIMFSNKMAR
LGKGYMFKSKSMKLRTQIPAEMLASIDLKYFNESTRKKIEKIRPLLIDGT
VSLSPGMMMGMFNMLSTVLGVSILNLGQKKYTKTTYWWDGLQSSDDFALI
VNAPNHEGIQAGVDRFYRTCKLVGINMSKKKSYINRTGTFEFTSFFYRYG
FVANFSMELPSFGVSGINESADMSIGVTVIKNNMINNDLGPATAQLALQL
FIKDYRYTYRCHRGDTQIQTRRSFELKKLWEQTRSKAGLLVSDGGPNLYN
IRNLHIPEVCLKWELMDEDYQGRLCNPLNPFVSHKEIESVNNAVVMPAHG
PAKSMEYDAVATTHSWIPKRNRSILNTSQRGILEDEQMYQKCCNLFEKFF
PSSSYRRPVGISSMVEAMVSRARIDARIDFESGRIKKEEFAEIMKICSTI
EELRRQK

SEQ ID NO: 2
MDVNPTLLFLKIPAQNAISTTFPYTGDPPYSHGTGTGYTMDTVNRTHQYS
EKGKWTTNTETGAPQLNPIDGPLPEDNEPSGYAQTDCVLEAMAFLEESHP
GIFENSCLETMEVVQQTRVDKLTQGRQTYDWTLNRNQPAATALANTIEVF
RSNGLTANESGRLIDFLKDVMESMNKEEIEITTHFQRKRRVRDNMTKKMV
TQRTIGKKKQRLNKRGYLIRALTLNTMTKDAERGKLKRRAIATPGMQIRG
FVYFVETLARSICEKLEQSGLPVGGNEKKAKLANVVRKMMTNSQDTEISF
TITGDNTKWNENQNPRMFLAMITYITRNQPEWFRNILSMAPIMFSNKMAR
LGKGYMFESKRMKIRTQIPAEMLASIDLKYFNESTKKKIEKIRPLLIDGT
ASLSPGMMMGMFNMLSTVLGVSILNLGQKKYTKTIYWWDGLQSSDDFALI
VNAPNHEGIQAGVDRFYRTCKLVGINMSKKKSYINKTGTFEFTSFFYRYG
FVANFSMELPSFGVSGVNESADMSIGVTVIKNNMINNDLGPATAQMALQL
```

-continued

SEQUENCES

```
FIKDYRYTYRCHRGDTQIQTRRSFELKKLWDQTQSKVGLLVSDGGPNLYN
IRNLHIPEVCLKWELMDDDYRGRLCNPLNPFVSHKEIDSVNNAVVMPAHG
PAKSMEYDAVATTHSWIPKRNRSILNTSQRGILEDEQMYQKCCNLFEKFF
PSSSYRRPVGISSMVEAMVSRARIDARVDFESGRIKKEEFSEIMKICSTI
EELRRQK

SEQ ID NO: 3
MDVNPTLLFLKVPAQNAISTTFPYTGDPPYSHGTGTGYTMDTVNRTHQYS
ERGKWTTNTETGAPQLNPIDGPLPEDNEPSGYAQTDCVLEAMAFLEESHP
GIFENSCLETMEAVQQTRVDKLTQGRQTYDWTLNRNQPAATALANTIEVF
RSNGLTANESGRLIDFLKDVMESMDKEEMEITTHFQRKRRVRDNMTKKMV
TQRTIGKKKQRVNKRGYLIRALTLNTMTKDAERGKLKRRAIATPGMQIRG
FVYFVETLARSICEKLEQSGLPVGGNEKKAKLANVVRKMMTNSQDTELSF
TITGDNTKWNENQNPRMFLAMITYITKNQPEWFRNILSIAPIMFSNKMAR
LGKGYMFESKKMKLRTQIPAEMLASIDLKYFNESTRKKIEKIRPLLIDGT
ASLSPGMMMGMFNMLSTVLGVSILNLGQKKYTKTTYWWDGLQSSDDFALI
VNAPNHEGIQAGVDRFYRTCKLVGINMSKKKSYINKTGTFEFTSFFYRYG
FVANFSMELPSFGVSGINESADMSIGVTVIKNNMINNDLGPATAQMALQL
FIKDYRYTYRCHRGDTQIQTRRSFEIKKLWDQTQSRAGLLVSDGGPNLYN
IRNLHIPEVCLKWELMDENYRGRLCNPLNPFVSHKEIESVNNAVVMPAHG
PAKSMEYDAVATTHSWIPKRNRSILNTSQRGILEDEQMYQKCCNLFEKFF
PSSSYRRPIGISSMVEAMVSRARIDARIDFESGRIKKEEFSEIMRICSTI
EELRRQK

SEQ ID NO: 4
MDVNPTLLFLKVPAQNAISTTFPYTGDPPYSHGTGTGYTMDTVNRTHQYS
EKGRWTTNTETGAPQLNPIDGPLPEDNEPSGYAQTDCVLEAMAFLEESHP
GLFENSCLETMEVVQQTRVDKLTQGRQTYDWTLNRNQPAATALANTIEVF
RSNGLTANESGRLIDFLKDVMESMDKEEMEITTHFQRKRRVRDNMTKKMV
TQRTIGKKKQKLTKKSYLIRALTLNTMTKDAERGKLKRRAIATPGMQIRG
FVHFVEALARSICEKLEQSGLPVGGNEKKAKLANVVRKMMTNSQDTELSF
TVTGDNTKWNENQNPRIFLAMITYITRNQPEWFRNVLSIAPIMFSNKMAR
LGKGYMFESKSMKLRTQIPAEMLANIDLKYFNESTRKKIEKIRPLLIEGT
ASLSPGMMMGMFNMLSTVLGVSILNLGQKRYTKTTYWWDGLQSSDDFALI
VNAPNHEGIQAGVDRFYRTCKLVGINMSKKKSYINRTGTFEFTSFFYRYG
FVANFSMELPSFGVSGINESADMSIGVTVIKNNMINNDLGPATAQMALQL
FIKDYRYTYRCHRGDTQIQTRRSFELKKLWEQTRSKAGLLVSDGGPNLYN
IRNLHIPEVGLKWELMDEDYQGRLCNPLNPFVSHKEVESVNNAVVMPAHG
PAKSMEYDAVATTHSWIPKRNRSILNTSQRGILEDEQMYQKCCTLFEKFF
PSSSYRRPVGISSMMEAMVSRARIDARIDFESGRIKKEEFAEIL

SEQ ID NO: 5
     1   atggatgtca atccgacctt acttttcttg aaagttccag
         cgcaaaatgc cataagtact
    61   acattccctt atactggaga tcctccatac agccatggaa
         caggaacagg atacaccatg
   121   gacacagtca acagaacaca tcaatattca gaaaagggga
         agtggacaac aaacacggaa
   181   actggagcgc accaacttaa cccaattgat ggaccactac
         ctgaggacaa tgaaccaagt
   241   ggatatgcac aaacagactg cgtcctggaa gcaatggctt
         tccttgaaga atcccaccca
   301   ggaatctttg aaaactcgtg tcttgaaacg atggaagtta
         ttcaacaaac aagagtggac
   361   aaactgaccc aaggtcgtca gacctatgat tggacattga
         acagaaatca gccggctgca
   421   actgcgctag ccaacactat agaggtcttc agatcgaatg
         gcctgacagc taatgaatcg
   481   ggaaggctaa tagatttcct caaggatgtg atagaatcaa
         tggataaaga ggagatggaa
   541   atcacaacac acttccaaag aaaaagaaga gtaagagaca
         acatgaccaa gaaaatggtc
   601   acacaacgaa caataggaaa gaagaagcaa agattgaaca
         agagaagcta tctaataaga
   661   gcactgacat tgaacacaat gactaaagat gcagagagag
         gtaaattaaa gagaagagca
   721   attgcaacac ccggtatgca gatcagaggg ttcgtgtact
         ttgtcgaaac actagcgaga
   781   agtatttgtg agaagcttga acagtctggg cttccggttg
         gaggtaatga aaagaaggct
   841   aaactggcaa atgttgtgcg aaaaatgatg actaattcac
         aagacacaga gctctctttc
   901   acaattactg gagacaatac caaatggaat gagaatcaaa
         atcctcggat gttcctggcg
   961   atgataacat acatcacaag aaatcaacct gaatggttta
         gaaacgtcct gagcatcgca
```

| | |
|---|---|
| 1021 | cctataatgt tctcaaataa aatggcaaga ctagggaaag gatacatgtt caaaagcaag |
| 1081 | agcatgaagc tccgaacaca aataccagca gaaatgctag caagtattga cctgaaatac |
| 1141 | tttaatgaat caacaagaaa gaaaatcgag aaaataaggc ctctcctaat agatggcaca |
| 1201 | gtctcattga gtcctgaact gatgatgggc atgttcaaca tgctaagtac agtcttagga |
| 1261 | gtctcaatcc tgaatcttga caaaagaag tacaccaaaa caacatactg gtgggacgga |
| 1321 | ctccaatcct ctgatgactt cgccctcata gtgaatgcac caaatcatga gggaatacaa |
| 1381 | gcaggggtgg atagattcaa cagaacctgc aagctagtcg gaatcaatat gagcaaaaag |
| 1441 | aagtcctaca taaataggac agggacatttt gaattcacaa gcttttttcta tcgctatgga |
| 1501 | tttgtagcca attttagcat ggagctgccc agctttggag tgtctggaat taatgaatcg |
| 1561 | gctgatatga gcattgggt aacagtgata agaacaaca tgataaacaa tgaccttgga |
| 1621 | ccagcaacag cccaactggc tcttcaacta ttcatcaaag actacagata tacgtaccgg |
| 1681 | tgccacagag gagacacaca aattcagaca aggagatcat tcgagctaaa gaagctgtgg |
| 1741 | gagcaaaccc gctcaaaggc aggactttg gtttcggatg gaggaccaaa cttatacaat |
| 1801 | atccggaatc tccacattcc agaagtctgc ttgaagtggg agctaatgga tgaagactat |
| 1861 | caggggagc tttgtaatcc cctgaatcca tttgtcagtc ataaggagat tgagtctgta |
| 1921 | aacaatgctg tggtaatgcc agctcacggt ccagccaaga gcatggaata tgatgctgtt |
| 1981 | gctactacac actccctgaa cccctaagagg aaccgctcca ttctcaacac aagccaaggg |
| 2041 | ggaattcttg aagatgaaca gatgtatcag aagtgttgca atctattcga gaaattcttc |
| 2101 | cctagcagtt cgtacagagg accagttgga atttccagca tggtggaggc catggtgtct |
| 2161 | agggcccga ttgatgcacg gattgacttc gagtctggac ggattaagaa agaggagttc |
| 2221 | gctgagatca tgaagatctg ttccaccatt gaagagctca gacggcaaaa atag |

SEQ ID NO: 6
MERIKELRNLMSQSRTREILTKTTVDHMAIIKKYTSGRQEKNPSLRMKWM
MAMKYPITADKRITEMIPERNEQGQTLWSKMSDAGSDRVMVSPLAVTWWN
RNGPMTSTVHYPKIYKTYFEKVERLKHGTFGPVHFRNQVKIRRRVDINPG
HADLSAKEAQDVIMEVVFPNEVGARILTSESQLTITKEKKEELQDCKISP
LMVAYMLERELVRKTRFLPVAGGTSSVYIEVLHLTQGTCWEQMYTPGGEV
RNDDVDQSLIIAARNIVRRAAVSADPLASLLEMCHSTQIGGTRMVDILRQ
NPTEEQAVEICKAAMGLRISSSFSFGGFTFKRTSGSSVKREEEVLTGNLQ
TLKIRVHEGYEEFTMVGKRATAILRKATRRLIQLIVSGRDEQSIAEAIIV
AMVFSQEDCMIKAVRGDLNFVNRANQRLNPMHQLLRHFQKDAKVLFQNWG
IEHIDNVMGMIGVLPDMTPSTEMSRGVRVSKMGVDEYSSAERVVVSIDR
FLRVRDQRGNVLLSPEEVSETQGTEKLTITYSSSMMWEINGPESVLVNTY
QWIIRNWETVKIQWSQNPTMLYNKMEFEPFQSLVPKAIRGQYSGFVRTLF
QQMRDVLGTFDTTQIIKLLPFAAAPPKQSRMQFSSLTVNVRGSGMRILVR
GNSPIFNYNKTTKRLTILGKDAGTLTEDPDEGTSGVESAVLRGFLILGKE
DRRYGPALSINELSNLAKGEKANVLIGQGDVVLVMKRKRNSSILTDSQTA
TKRIRMAIN

SEQ ID NO: 7
IKELWDLMSQSRTREILTKTTVDHMAIIKKYTSGRQEKNPALRMKWMMAM
KYPITADKRIMEMIPERNEQGQTLWSKTNDAGSDRVMESPLAVTWWNRNG
PTTSTVHYPKVYKTYFEKVERLKHGTFGPVHFRNQVKIRRRVDMNPGHAD
LSAKEAQDVIMEVVFPNEVGARILTSESQLTITKEKREELKNCNIAPLMV
AYMLERELVRKTRFLPVAGGTSSVYIEVLHLTQGTCWEQMYTPGGEVRND
DVDQSLIIAVGNIVRRATVSADPLASLLEMCHSTQIGGVRMVDILKQNPT
EEQAVDICKAAMGLKISSSFSFGGFTFKRTKGSSVKREEEVLTGNLQTLK
IKVHEGYEEFTMVGRRATAILRKATRIMIQLIVSGRDEQSIAEAIIVAMV
FSQEDCMIKAVRGDLNFVNRANQRLNPMHQLLRHFQKDAKVLFQNWGTEP
IDNVMGMIGILPDMTPSTEMSLRGVRVSKMGVDEYSSTERVVVSIDRFLR
VRDQRGNVLLSPEEVSETQGMEKLTITYSSSMMWEINGPESVLVNTYQWI
IRNWETVKIQWSQEPTMLYNKMEFEPFQSLVPKAARSQYSGFVRTLFQQM
RDVLGTFDTVQIIKLLPFAAAPPEQSRMQFSSLTVNVRGSGMRILVRGNS
PAFNYNKTTKRLTILGKDAGALTEDPDEGTAGVESAVLRGFLILGKEDKR
YGPALSINELSNLTKGEKANVLIGQGDVVLVMKRKRDSSILTDSQTATKR
I

SEQ ID NO: 8
MERIKELRDLMSQSRTREILTKTTVDHMAIIKKYTSGRQEKNPALRMKWM
MAMKYPITADKRIMEMIPERNEQGQTLWSKTNDAGSDRVMVSPLAVTWWN
RNGPTTSTVHYPKVYKTYFEKVERLKHGTFGPVHFRNQVKIRRRVDINPG
HADLSAKEAQDVIMEVVFPNEVGARILTSESQTTITKEKKKELQDCKIAP
LMVAYMLERELVRKTRFLPVAGGTSSVYIEVLHLTQGTCWEQMYTPGGEV
RNDDVDQSLIIAARNIVRRATVSADPLASLLEMCHSTQIGGIRMVDILRQ
NPTEEQAVDICKAAMGLRISSSFSFGGFTFKRTSGSSVKREEEVLTGNLQ
TLKIRVHEGYEEFTMVGRRATAILRKATRRLIQLIVSGKDEQSIAEAIIV
AMVFSQEDCMIKAVRGDLNFVNRANQRLNPMHQLLRHFQKDAKVLFQNWG
IEPIDNVMGMIGILPDMTPSTEMSLRGVRVSKMGVDEYSSTERVVVSIDR
FLRVRDQRGNVLLSPEEVSETQGTEKLTITYSSSMMWEINGPESVLVNTY
QWIIRNWENVKIQWSQDPTMLYNKMEFEPFQSLVPKAARGQYSGFVRLF
QQMRDVLGTFDTVQIIKLLPFAAAPPKQSRMQFSSLTVNVRGSGMRIVVR
GNSPVFNYNKATKRLTVLGKDAGALMEDPDEGTAGVESAVLRGFLILGKE
DKRYGPALSINELSNLAKGEKANVLIGQGDVVLVMKRKRDSSILTDSQTA
TKRIRMAIN

SEQ ID NO: 9
SRTREILTKTTVDHMAIIKKYTSGRQEKNPSLRMKWMMAMKYPITADKRI
MEMIPERNEQGQTLWSKTNDAGSNRVMVSPLAVTWWNRNGPTTSTIHYPK
VYKTYFEKVERLKHGTFGPVHFRNQVKIRRRVDVNPGHADLSAKEAQDVI
MEVVFPNEVGARILTSESQLAITKEKKEE

SEQ ID NO: 10
MFDFVRQCFNPMIVELAFKTMKEYGEDLKIETNKFAAICTHLEVCFMYSD
FHFINEQGESIIVELGDPNALLKHRFEIIEGRDRTMAWTVVNSICNTTGA
EKPKFLPDLYDYKENRFIEIGVTRREVHIYYLEKANKIKSEKTHIHIFSF
TGEEMATKADYTLDEESRARIKTRLFTIRQEMASRGLWDSFRQSERGEET
IEERFEITGTMRKLADQSLPPNFSSLENFRAYVDGFEPNGYIEGKLSQMS
KEVNARIEPFLKTTPRPLRLPNGPPCSQRSKFLLMDALKLSIEDPSHEGE
GIPLYDAIKCMRTFFGWKEPNVVKPFLEKGINPNYLLSWKQVLAELQDIE
NEEKIPKTKNMKKTSQLKWALGENMAPEKVDFDDCKDVGDLKQYDSDEPE
LRSLASWIQNEFNKACELTDSSWIELDEIGEDVAPIEHIASMRRNYFTSE
VSHCRATEYIMKGVYINTALLNASCAAMDDFQLIPMISKCRTKEGRRKTN
LYGFIIKGRSHLRNDTDVVNFVSMEFSLTDPRLEPHKWEKYCVLEIGDML
IRSAIGQVSRPMFLYVRTNGTSKIKMKWGMEMRRCLLQSLQQIESMFEAE
SSVKEKDMTKEFFENKSETWPIGESPKGVEESSIGKVCRTLLAKSVFNSL
YASPQLEGFSAESRKLLLIVQALRDNLEPGTFDLGGLYEAIEECLINDPW
VLLNASWFNSFLTHALS

What is claimed is:

1. A modified influenza A virus comprising a PB1 polymerase comprising one or more mutations selected from the group consisting of a leucine to glutamic acid, aspartic acid or asparagine substitution at an amino acid corresponding to position 319 (L319E/D/N) of SEQ ID NO: 1, a threonine to glutamic acid, aspartic acid, glutamine or asparagine substitution at an amino acid corresponding to position 323 (T323E/D/Q/N) of SEQ ID NO: 1; and an isoleucine to glutamic acid, aspartic acid, glutamine or asparagine substitution at an amino acid corresponding to position 342 (I342E/D/Q/N) of SEQ ID NO: 1.

2. The virus of claim 1, wherein the PB1 polymerase comprises a leucine to glutamic acid substitution (L319E).

3. The virus of claim 1, wherein the PB1 polymerase comprises a leucine to asparagine substitution (L319N).

4. The virus of claim 1, wherein the PB1 polymerase further comprises one or more mutations selected from the group consisting of a lysine to glutamic acid substitution at an amino acid corresponding to position 391 (K391E) of SEQ ID NO: 1, a glutamic acid to glycine substitution at an amino acid corresponding to position 581 (E581G) of SEQ ID NO: 1 and an alanine to threonine substitution at an amino acid corresponding to position 661 (A661T) of SEQ ID NO: 1.

5. The virus of claim 1, wherein the virus further comprises a PB2 polymerase comprising an asparagine to serine substitution at position 265 (N265S).

6. The virus of claim 1, wherein the virus further comprises an influenza virus nucleoprotein (NP) comprising an aspartic acid to glycine substitution at position 34 (D34G).

7. The virus of claim 1, wherein the influenza A virus is selected from the group consisting of an H2N2 virus, an H3N2 virus, an H1N1 virus, an H9N2 virus and an H5N1 virus.

8. The virus of claim 1, wherein the influenza A virus is (A/Puerto Rico/8/34/H1 N1)(PR8), (A/California/04/2007 H1N1) or (A/Ann Arbor/6/60 H2N2).

9. The virus of claim 1, wherein the virus is a live attenuated influenza A virus with reduced growth from about 37° C. to about 39° C., as compared to an influenza A virus comprising a PB1 polymerase lacking one or more mutations selected from the group consisting of a leucine to glutamic acid, aspartic acid or asparagine substitution at an amino acid corresponding to position 319 (L319E/D/N) of SEQ ID NO: 1, a threonine to glutamic acid, aspartic acid, glutamine or asparagine substitution at an amino acid corresponding to position 323 (T323E/D/Q/N) of SEQ ID NO: 1; and an isoleucine to glutamic acid, aspartic acid, glutamine or asparagine substitution at an amino acid corresponding to position 342 (I342 E/D/Q/N) of SEQ ID NO: 1.

10. An immunogenic composition comprising the virus of claim 1 and a pharmaceutically acceptable carrier.

11. A method for eliciting an immune response against an influenza virus in a subject, comprising administering an effective dose of the immunogenic composition of claim 10 to the subject.

12. A method of treating or reducing the risk of influenza infection in a subject, comprising administering to a subject with an influenza infection or at risk of exposure to an influenza infection an effective dose of the immunogenic composition of claim 10.

13. A recombinant nucleic acid encoding a PB1 polymerase of an influenza A virus, wherein the nucleic acid encodes a PB1 polymerase having one or more mutations selected from the group consisting of a leucine to glutamic acid, aspartic acid or asparagine substitution at an amino acid corresponding to position 319 (L319E/D/N) of SEQ ID NO: 1, a threonine to glutamic acid, aspartic acid, glutamine or asparagine substitution at an amino acid corresponding to position 323 (T323E/D/Q/N) of SEQ ID NO: 1; and an isoleucine to glutamic acid, aspartic acid, glutamine or asparagine substitution at an amino acid corresponding to position 342 (I342E/D/Q/N) of SEQ ID NO: 1.

14. A recombinant nucleic acid encoding a PB1 polymerase of an influenza A virus wherein the nucleic acid encodes a PB1 polymerase comprising one or more mutations selected from the group consisting of a leucine to glutamic acid, aspartic acid or asparagine substitution at an amino acid corresponding to position 319 (L319E/D/N) of SEQ ID NO: 1, a threonine to glutamic acid, aspartic acid, glutamine or asparagine substitution at amino acid corresponding to position 323 (T323E/D/Q/N) of SEQ ID NO: 1; a serine to glutamic acid, aspartic acid, glutamine or asparagine substitution at an amino acid corresponding to position 338 (S338E/D/Q/N) and an isoleucine to glutamic acid, aspartic acid, glutamine or asparagine substitution at an amino acid corresponding to position 342 (I342E/D/Q/N) of SEQ ID NO: 1; and one or more mutations selected from the group consisting of a lysine to glutamic acid substitution at an amino acid corresponding to position 391 (K391E) of SEQ ID NO: 1, a glutamic acid to glycine substitution at an amino acid corresponding to position 581 (E581G) of SEQ ID NO: 1 and an alanine to threonine substitution at an amino acid corresponding to position 661 (A661T) of SEQ ID NO: 1.

15. A vector comprising the nucleic acid of claim 13.

16. A method of producing the influenza virus of claim 1, comprising:
   a) transfecting a population of host cells with one or more vectors comprising
      (i) nucleic acid sequences encoding the internal genome segments of an influenza A virus and
      (ii) a nucleic acid encoding a PB1 polymerase comprising one or more mutations selected from the group consisting of a leucine to glutamic acid, aspartic acid or asparagine substitution at an amino acid corresponding to position 319 (L319E/D/N) of SEQ ID NO: 1, a threonine to glutamic acid, aspartic acid, glutamine or asparagine substitution at an amino acid corresponding to position 323 (T323E/D/Q/N) of SEQ ID NO: 1; and an isoleucine to glutamic acid, aspartic acid, glutamine or asparagine substitution at an amino acid corresponding to position 342 (I342 E/D/Q/N) of SEQ ID NO: 1;

b) culturing the host cells; and c) recovering the influenza A virus.

17. The method of claim 16, wherein the nucleic acid encoding the PB1 polymerase encodes a PB1 polymerase comprising one or more mutations selected from the group consisting of a leucine to glutamic acid, aspartic acid or asparagine substitution at an amino acid corresponding to position 319 (L319E/D/N) of SEQ ID NO: 1, a threonine to glutamic acid, aspartic acid, glutamine or asparagine substitution at an amino acid corresponding to position 323 (T323E/D/Q/N) of SEQ ID NO: 1; a serine to glutamic acid, aspartic acid, glutamine or asparagine substitution at an amino acid corresponding to position 338 (S338 E/D/Q/N) of SEQ ID NO: 1 and an isoleucine to glutamic acid, aspartic acid, glutamine or asparagine substitution at an amino acid corresponding to position 342 (I342 E/D/Q/N) of SEQ ID NO: 1; and one or mutations selected from the group consisting of a glutamic acid to glycine substitution at an amino acid corresponding to position 581 (E581G) of SEQ ID NO: 1 and an alanine to threonine substitution at an amino acid corresponding to position 661 (A661T) of SEQ ID NO: 1.

18. The method of claim 16, wherein the one or more vectors further comprise a nucleic acid encoding a PB2 polymerase comprising a N265S mutation.

19. The method of claim 16, further comprising transforming the cells with a nucleic acid encoding an influenza virus nucleoprotein (NP) comprising an aspartic acid to glycine substitution at position 34 (D34G).

20. The method of claim 16, wherein the influenza A virus is selected from the group consisting of an H2N2 virus, an H3N2 virus, an H1N1 virus, an H9N2 virus and an H5N1 virus.

21. The method of claim 16, wherein the cells are Vero cells, MDCK cells or CEK cells.

22. A method for producing an influenza immunogen comprising:

(a) infecting a population of cells with the virus of claim 1;

(b) culturing the cells;

(c) harvesting the virus from the culture of step b); and (d) preparing an immunogen with the harvested virus.

23. The method of claim 22, wherein the cells are mammalian cells or avian cells.

24. A population of isolated cells comprising the virus of claim 1.

* * * * *